United States Patent [19]
Voorhees et al.

[11] Patent Number: 5,643,681
[45] Date of Patent: Jul. 1, 1997

[54] BIOCOMPATIBLE COATED ARTICLE

[75] Inventors: Marc Voorhees, Arvada; Lloyd Forrestal, Boulder, both of Colo.; Harold Fisher, Charlotte, N.C.

[73] Assignee: Cobe Laboratories, Inc., Lakewood, Colo.

[21] Appl. No.: 473,723

[22] Filed: Jun. 7, 1995

Related U.S. Application Data

[63] Continuation of Ser. No. 227,955, Apr. 15, 1994, abandoned.

[51] Int. Cl.$^6$ .............................. B32B 27/32; B32B 27/36
[52] U.S. Cl. ................ 428/483; 428/315.5; 428/315.9; 428/319.7; 428/447; 428/451; 428/480
[58] Field of Search ............... 428/308.4, 315.5, 428/315.9, 319.3, 319.7, 423.7, 425.5, 447, 451, 480, 483

[56] References Cited

U.S. PATENT DOCUMENTS

| | | | |
|---|---|---|---|
| 3,651,616 | 3/1972 | Blanchard et al. | 55/16 |
| 4,636,552 | 1/1987 | Gay et al. | 525/63 |
| 4,663,413 | 5/1987 | Ward et al. | 528/26 |
| 4,675,361 | 6/1987 | Ward, Jr. et al. | 525/92 |
| 4,872,867 | 10/1989 | Joh | 604/269 |
| 4,929,510 | 5/1990 | Ruckenstein et al. | 428/520 |
| 4,970,765 | 11/1990 | Canivenc et al. | 528/15 |
| 5,179,142 | 1/1993 | Ono et al. | 524/35 |

FOREIGN PATENT DOCUMENTS

| | | |
|---|---|---|
| 19 44 969 | 3/1970 | Germany. |
| 42 17 165 | 8/1993 | Germany. |

OTHER PUBLICATIONS

Zisman, W.A. (1964) *Adv. Chem. Ser.* 43.
Lovinger et al. (1993) "Morphology and Properties of Polycaprolactone–Poly(dimethyl siloxane)–Polycaprolactone Triblock Copolymers," *J. Polymer Sci. Part B (Polymer Physics)* 31:115–123.
Gemmell et al. (1995) *J. lab. Clin. Med.* 125:276–287.
Clarson and Semlyn (eds.) (1993) *Siloxane Polymers*, "Radiation Cross–Linking of Siloxanes," pp. 606–609.

*Primary Examiner*—D. S. Nakarani
*Attorney, Agent, or Firm*—Greenlee, Winner and Sullivan, P.C.

[57] ABSTRACT

The biocompatibility of polymeric and metallic articles used in contact with blood can be substantially improved by coating the articles as described. The coating materials are triblock copolymers of the polylactone-polysiloxane-polylactone type. Optimum biocompatibility is provided by a coating of optimum surface concentration. Porous membranes can be coated as described, providing improved biocompatibility of blood oxygenators, hemodialyzers and the like.

12 Claims, 14 Drawing Sheets

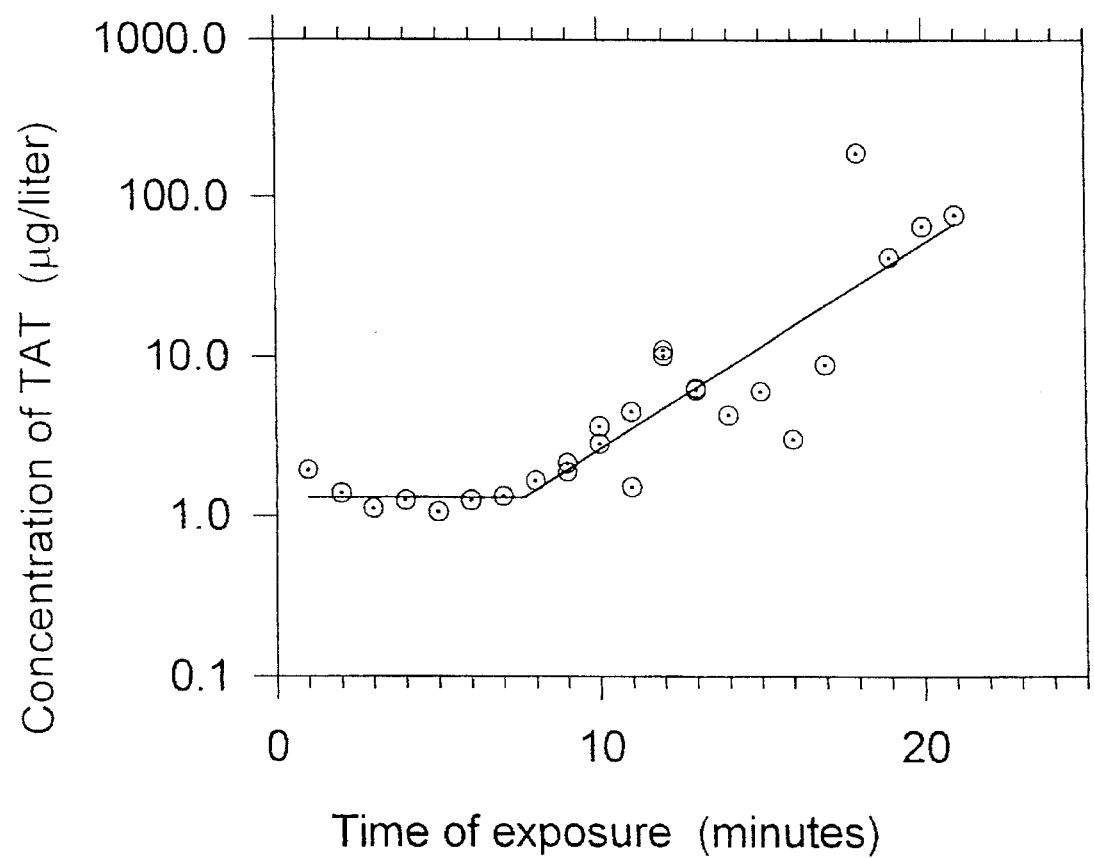

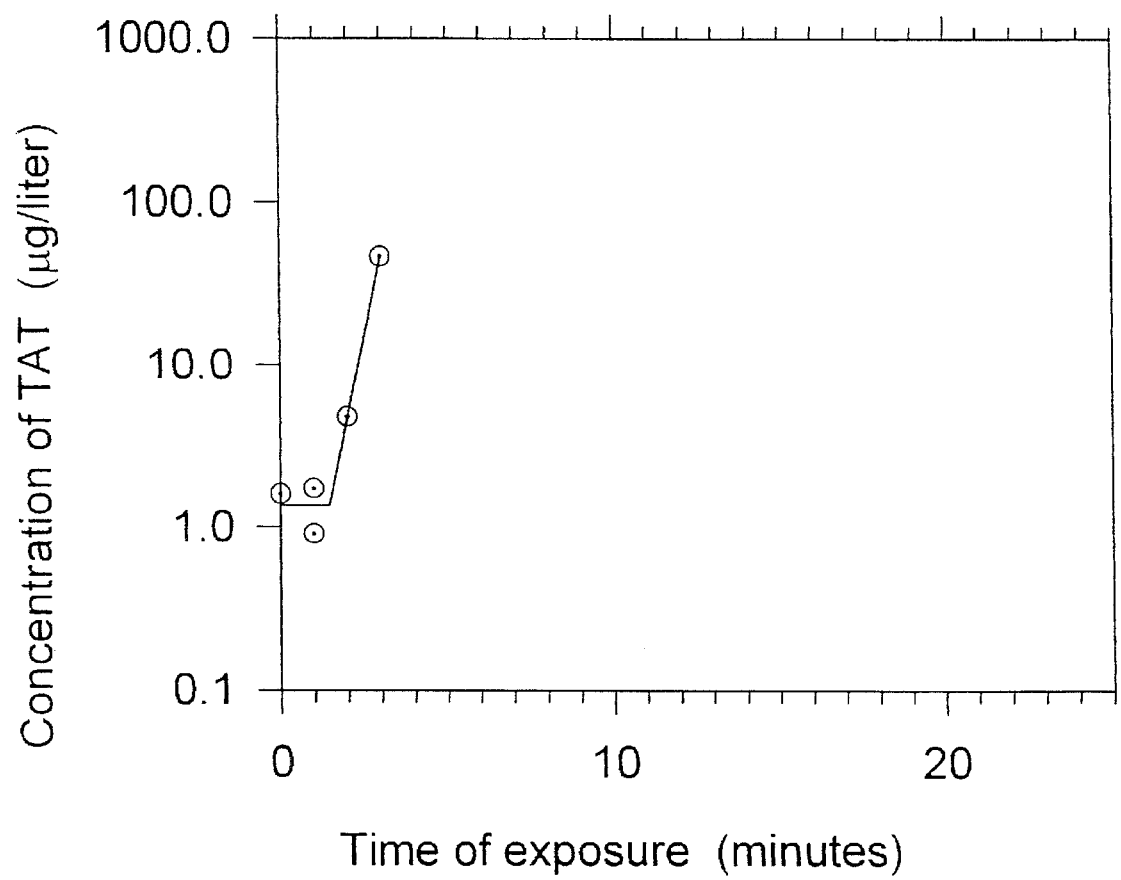

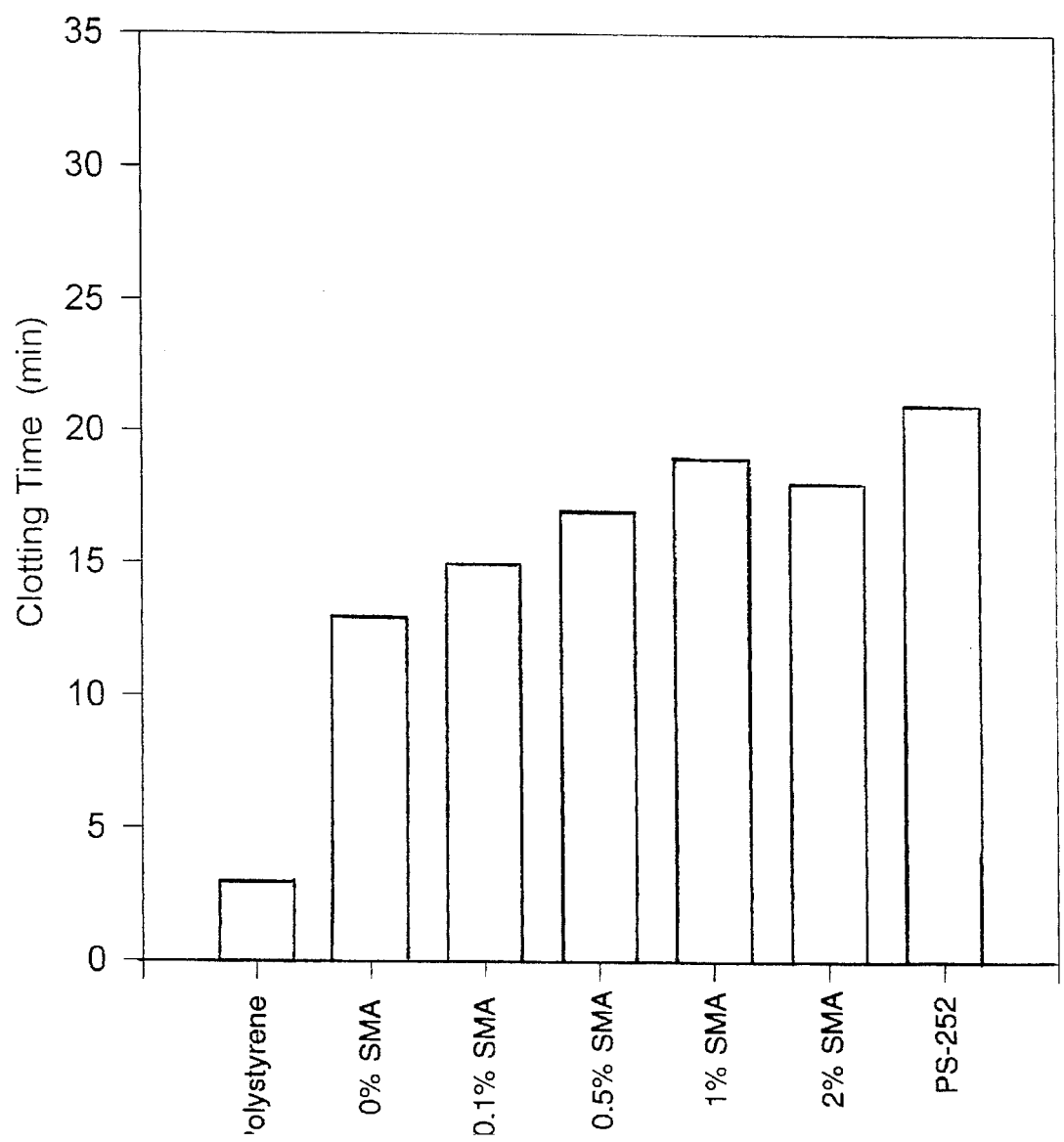

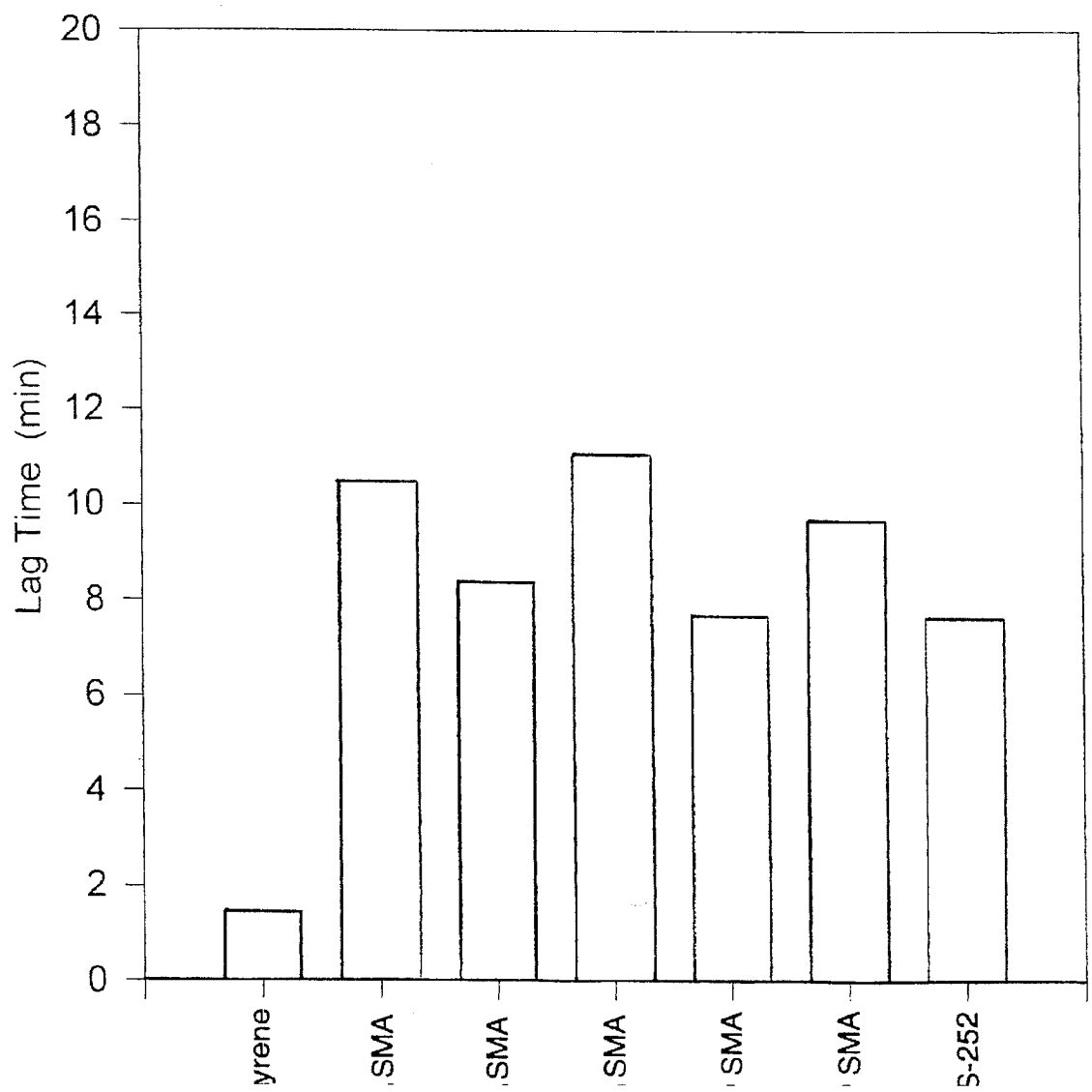

BIOCOMPATIBLE COATED ARTICLE

Reference to Related Application

This application is a continuation of U.S. application Ser. No. 08/227,955 filed Apr. 15, 1994, this application is also a continuation of International Application Ser. No. PCT/US95/04584 filed Apr. 14, 1995.

FIELD OF THE INVENTION

The invention is directed to improved materials for medical devices, in particular to materials intended for contacting blood and live cells, where adverse physiological reactions such as clot initiation must be minimized or eliminated. Such biocompatible materials are useful in extracorporeal blood oxygenation devices, hemodialysis devices, and the like.

BACKGROUND AND PRIOR ART

A basic problem in the construction of medical devices having components that must contact blood and other physiological fluids is that materials with good mechanical and structural properties have rather poor biocompatibility, while highly biocompatible materials have poor structural properties. Biocompatibility is itself a multi-faceted problem which has different aspects depending on the type of device, what tissues or fluids it contacts, and the length of contact time. In devices designed for hemodialysis or blood oxygenation, the materials are in contact with blood flowing through tubing, into containers, through heat exchangers and over membranes. The blood returns to the patient's body. The primary elements of biocompatibility are therefore to prevent initiating processes which can subsequently injure the patient, such as activation of clotting mechanisms, activation of the complement system, and initiation of inflammatory reactions. Materials must not be soluble in blood or other body fluids to avoid being carried permanently into the patient's body.

Although certain types of polymers, such as silicones and siloxanes, are known to possess many attributes of biocompatibility, there are no reliable physical correlates which enable one to predict biocompatibility with any degree of certainty. Generally, hydrophobic surfaces are more biocompatible than hydrophilic surfaces. Zisman's critical surface tension [Zisman, W. A. (1964) Adv. Chem. Ser. 43] has been used as a parameter to help assess potential biocompatibility. Materials with an optimum critical surface tension are frequently biocompatible, yet there are notable exceptions. For example, polyethylene and polypropylene have critical surface tensions well within the optimum range, but they are not predictably biocompatible. Other factors are also important. Without a clear understanding of the nature of these factors, biocompatibility remains unpredictable.

Because of the attractive structural properties of polyolefins and polyurethanes, various blending and co-polymerization techniques have been developed to impart greater biocompatibility. U.S. Pat. 4,872,867 discloses modifying a polyurethane with a water soluble polymer and crosslinking them in situ with a silane-type coupling-agent to form a cross-linked and intertwined polysiloxane network. U.S. Pat. 4,636,552 discloses a polydimethyl siloxane with polylactone side chains which are said to be useful for imparting biocompatibility when combined with a base polymer, or used to replace plasticizer. U.S. Pat. 4,929,510 discloses a diblock copolymer having a more hydrophobic block and a less hydrophobic block. A solution of the diblock copolymer in a solvent which swells the matrix polymer is used to introduce the diblock into an article of matrix polymer. Thereafter, the article is transferred to water, to force orientation of the incorporated diblock copolymer such that the more hydrophobic block is embedded in the matrix and the less hydrophobic block is exposed on the surface of the article. Examples of diblock copolymers included poly (ethyleneoxide-propylene oxide), N-vinyl-pyrrolidone-vinyl acetate and N-vinyl-pyrrolidone-styrene. U.S. Pat. Nos. 4,663,413 and 4,675,361 disclose segmented block copolymers, in particular polysiloxane-polycaprolactone linear block copolymers. The latter were incorporated into base polymer materials to modify the surface properties thereof. Although initially blended in bulk into the base polymer, the copolymer migrates to the surface to form an exceptionally thin, possibly a monolayer film which imparts the desired surface characteristic, specifically, biocompatibility.

Although numerous surface-modifying compositions have been disclosed in the art, their intended use has been as bulk formulation additives, as mixtures with base polymer, cross-linked within the polymer matrix, as substitutes for plasticizer or incorporated into the polymer matrix. The art has avoided coatings, in part because of increased manufacturing cost and difficulty of uniform application. For certain applications such as microporous membranes, application of a coating could adversely affect membrane properties by plugging membrane pores or otherwise degrading performance. In the case of microporous membranes made by a process of stretching polymer film stock, total surface area is expanded to the extent that the available surface concentration of surface modifiers added in conventional formulation processes is reduced to ineffectiveness. Providing a biocompatible surface for a microporous membrane remains a matter of critical importance, since the membrane has the largest surface area in contact with a patient's blood of any component of an oxygenator or hemodialysis unit. Another component with a large blood contact area is a heat exchanger, commonly fabricated of metal, used to maintain a desired extracorporeal blood temperature. Aluminum, titanium and stainless steel are all used for various sorts of blood-contacting devices. Aluminum is reactive with blood and is commonly coated with epoxy or polyurethane to prevent adverse reactions. Although less reactive than aluminum, both stainless steel and titanium have suboptimal biocompatibility in contact with blood.

From what is known of their properties as bulk additives, the triblock copolymers would be unlikely candidates for use as coatings since the blocks that normally anchor the copolymer within the base polymer matrix would be exposed on the surface. Nevertheless, as detailed herein, it has now been found that certain triblock copolymers can be applied as coatings to impart biocompatibility to polymeric surfaces. It has also been found unexpectedly that the same copolymers can be used to coat surfaces of other polymeric and metallic articles, imparting excellent biocompatibility to them. The same copolymers also improve the biocompatibility of polymer-coated metal surfaces, for example, aluminum coated with epoxy or polyurethane.

SUMMARY OF THE INVENTION

The invention provides porous membranes and other polymeric articles that are coated to improve the biocompatibility of the membrane or other article compared to the base polymeric composition of an uncoated membrane or article. The invention also provides metal flat sheets and metallic articles that are coated to improve the bicompatibility of the sheet or article compared to the uncoated metal sheet or article. The coating material is any of several triblock copolymers having a polysiloxane segment flanked by or end-capped with two polylactone segments. The coating thickness must be within an optimum range in order to provide optimum biocompatibility. The base polymeric composition or base metal can be any material from which porous membranes or other articles can be made. The invention is especially useful for microporous membranes used in extra-corporeal blood oxygenators where $O_2$ and $CO_2$ diffuse through the pores but $H_2O$ does not, and in hemodialysis membranes. In such devices blood contact with the membrane surfaces is maximized and the need for biocompatibility is at a premium. The invention is also useful for metallic surfaces in extracorporeal blood processing devices, for example, thermistor probes, and heat exchangers. Biocompatibility is measured herein by the reduced tendency to induce clotting enzyme activity, to induce kallikrein-like activity, to activate the complement cascade in blood and plasma exposures, induction of IL-1β by mononucleocytes, by platelet deposition in ex-vivo shunt studies, and by in vitro platelet activation tests.

BRIEF DESCRIPTION OF THE FIGURES

FIG. 5A: uncoated 316L stainless steel; FIG. 5B: 316L stainless steel dip-coated with a 0.1% SMA-423 solution; FIG. 5C: 316L stainless dip-coated with a 0.5% SMA-423 solution; FIG. 5D: 316L stainless steel dip-coated with a 1.0% SMA-423 solution; FIG. 5E: 316L stainless steel dip-coated with a 2.0% SMA-423 solution; FIG. 5F: PDMS (PS-252)-coated polystyrene; FIG. 5G: polystyrene (uncoated).

DETAILED DESCRIPTION OF THE INVENTION

Figure 1:
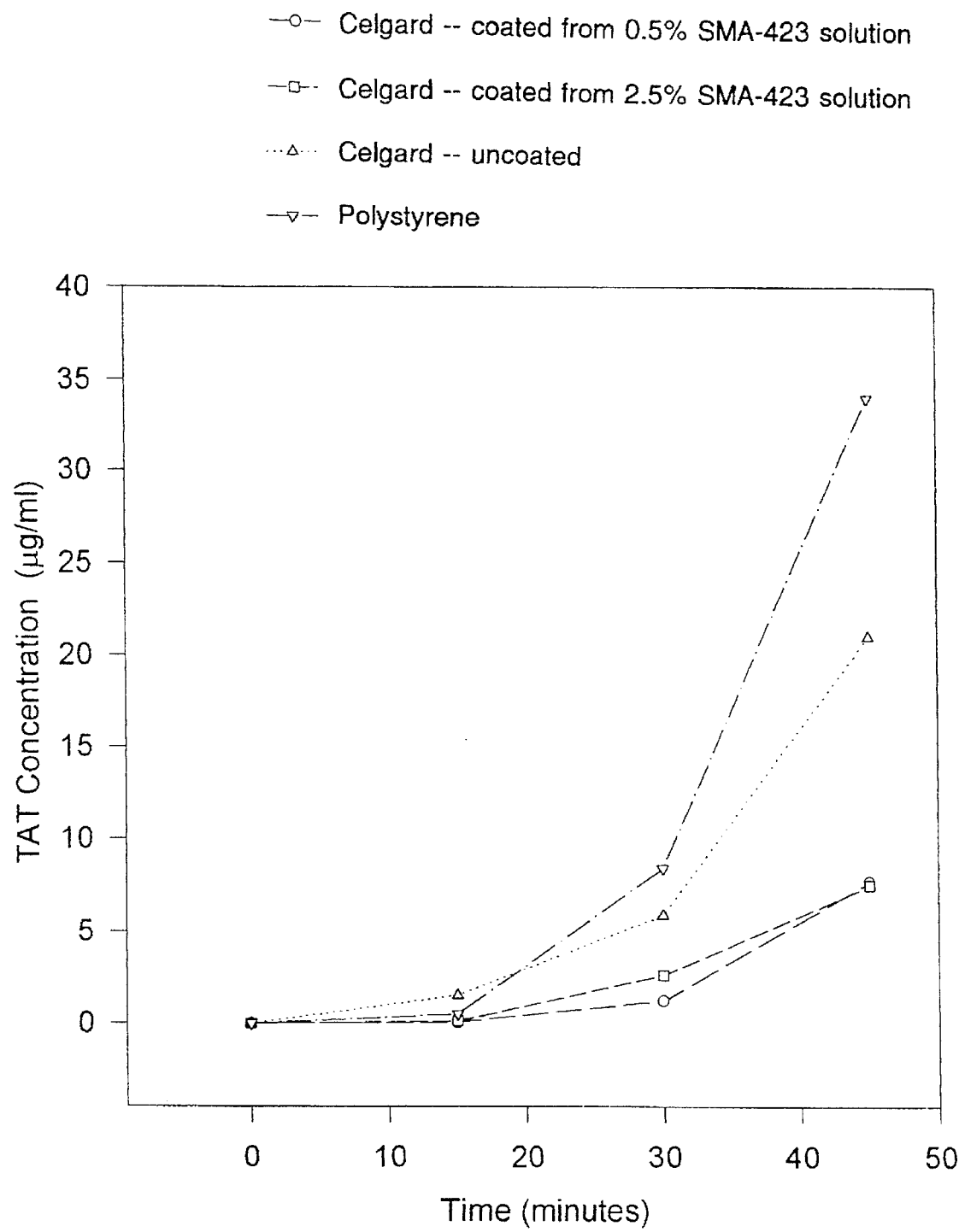
FIG. 1 is a graph of thrombin-antithrombin III (TAT) complex in human whole blood exposed to various microporous membranes for times indicated on the abscissa. Solid dots: Celgard membrane (Trademark Hoechst Celanese, Charlotte, N.C.) dip-coated with a 0.5% SMA-423 solution; Squares: Celgard membrane dip-coated with a 2.5% SMA-423 solution; Triangles: uncoated Celgard membrane; Triangles (inverted): Polystyrene plaque.
Figure 2:
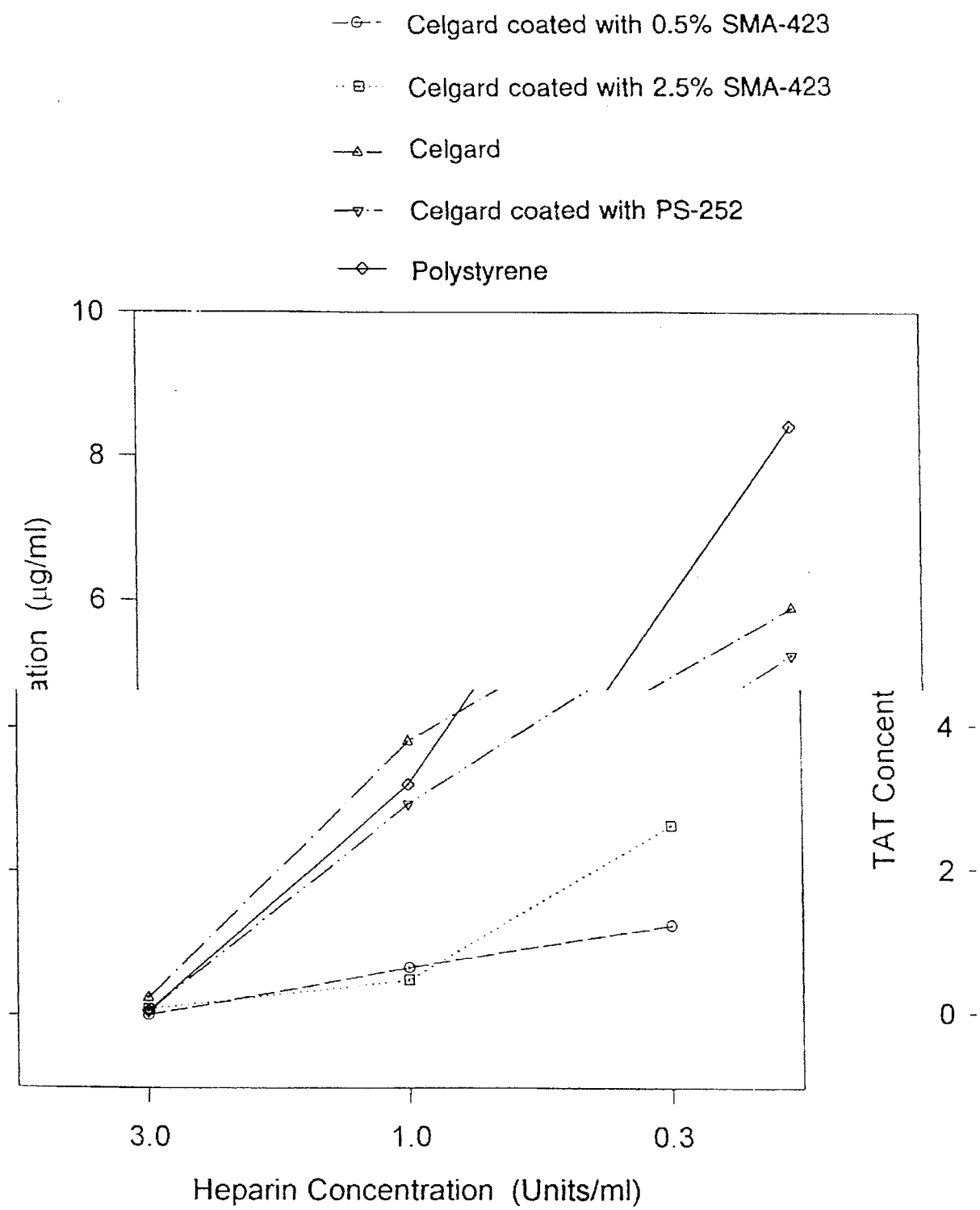
FIG. 2 is a graph of TAT complex in human whole blood containing varied concentrations of heparin, after 30 minute exposure to various microporous membranes. Dots, squares, and triangles in FIG. 1. Triangles (inverted): Celgard membrane with PS-252 silicone (United Chemical Technology, Bristol, Pa.); Diamonds: polystyrene plaque.

The coating materials of the present invention are triblock copolymers having a polysiloxane(S) block flanked by poly-lactone (L) blocks. The abbreviation LSL is used to designate such polylactone-polysiloxane-polylactone copolymers herein. Suitable triblock copolymers are commercially available, for example from Thoratec Laboratories, Berkeley, Calif., which provides a series of such polymers designated "SMA" in which the siloxane is dimethyl siloxane and the lactone is caprolactone. The nominal molecular weights (number average) of the polysiloxane blocks suitable for use herein range from about 1000 to about 5000, while the nominal molecular weights of the caprolactone blocks range from about 1000 to about 10,000. An LSL triblock copolymer having polycaprolactone blocks of 1000 and polysiloxane blocks of 1000 (SMA-411) has been shown to be usable, as has a copolymer having polycaprolactone blocks of 10,000 and polysiloxane blocks of 5000 (SMA-10-5-10). A lower molecular weight limit is conferred by the need to have a melting temperature above room temperature, and an upper limit is affected by practical considerations such as solubility, solution viscosity and tendency to fill in the membrane pores. Preferred coating material is provided by SMA-422 or SMA-423, having polycaprolactone blocks of 2000 nominal molecular weight and polysiloxane blocks of 2000 or 3000 nominal molecular weight, respectively. Physical properties conferred by the respective blocks and the effect of varying the relative sizes are well understood in the art, see, e.g. Lovinger, et al. (1993) *J. Polymer Sci.* Part B (*Polymer Physics*) 31: 115–123.

The porous membrane can be fabricated from any base polymer composition suitable for making porous membranes. Porous membranes have a variety of uses in medical devices. The pore size varies with the use. Such uses include dialysis, ultrafiltration, plasma separation, protein purification, blood oxygenation, hemodialysis, hemoconcentration, blood filters, and catheter sheaths. Certain dialysis membranes have pore sizes having dimensions of Angstroms and are permeable only to atoms and molecules of less than approximately 5000 molecular weight. "Microporous" membranes generally have pores dimensioned in microns and can be used for blood oxygenation. Still larger pores of 20μ–40μ are used in blood filter elements, designed to allow passage of blood cells but to exclude thrombi and other aggregates. Porous membranes are fabricated from various base polymers, by a variety of processes known in the art. The choice of base polymer and process of making is dictated to some extent by the size and type of pores desired. The biocompatibility of all such porous membranes is greatly enhanced by the coating materials and processes described herein.

Typical base polymers which may be utilized according to the present invention include polycarbonates, fluorocarbon polymers, polyurethanes, polysulfones, polyesters, polyethylenes, polypropylenes, polystyrenes, poly (acrylonitrile-butadiene-styrene), polybutadiene, polyisoprene, styrene-butadiene-styrene block copolymers, styrene-isoprene-styrene blockcopolymers, poly-(4-methylpentene), polyisobutylene, polymethylmethacrylate, polyvinylacetate, polyacrylonitrile, polyvinylchloride, polyethylene terephthalate, cellulose and its esters or derivatives, copolymers of the foregoing and the like. Porous membranes are fabricated by a variety of well-known techniques, any of which can be applied, as appropriate to the selected base polymer composition. For example, microporous membranes formed by a process of stretching polypropylene sheet stock, such as Celgard membranes (Trademark Hoechst Celanese, Charlotte, N.C.), are suitable for the invention. Such membranes have generally oblong pores having a minor diameter about 0.02 micron and a major diameter about 0.2 micron, and are permeable to $O_2$ and $CO_2$, making them suitable for blood oxygenation.

In addition to polymeric membranes and articles, the present invention contemplates a wide variety of biocompatible metallic surfaces and articles. Typical metal materials which may be utilized according to the present invention include stainless steel, aluminum, titanium, polymer-coated metals and the like.

A major deficiency of the base polymer compositions of porous membranes and the metal surfaces of extracorporeal blood processing devices lies in the fact that, to varying degrees, the materials are not biocompatible. Surprisingly, it has been found that substantial improvement in biocompatibility is obtained, without sacrificing $O_2/CO_2$ exchange capacity or dialysis capability, by coating a porous membrane with an LSL triblock copolymer of the type herein described. Thus, several unexpected findings are herein combined: that stable coatings are formed by LSL copolymers, that the coatings can be formed so as not to block the membrane pores essential for $O_2/CO_2$ exchange or for passage of ions and small molecules, and that biocompatibility is improved by the presence of the coating. Furthermore it has been shown that optimal biocompatibility results from a coating of optimum surface concentration. It is also unexpected to find that a stable LSL coating can also be applied to a metal surface. The process of coating is to be distinguished from blending, melt mixing, codissolving, copolymerization or other base formulation processes. Therefore, a coating is that which is applied by a post-fabrication surface application process.

A coating of LSL copolymer can be applied by any convenient technique for coating thin film materials, solid articles, melting and the like, including but not limited to dipping, spraying, passage through a coating bath and the like. By varying the process parameters, the surface concentration of the LSL coating polymer can be controlled. For example, in a dip-coating process, surface concentration can be controlled by varying the concentration of LSL in the dip solution. In a continuous passage process, which is more suitable for coating bulk quantities of membrane, surface concentration is regulated both by the concentration of LSL in the coating bath and by the rate of travel of the membrane stock through the bath. For coating membranes, it is preferred that the solvent be chosen so as not to dissolve the base polymer of the membrane. Optimal surface concentrations of SMA-422 and SMA-423 have been obtained by dipping Celgard membrane in a 0.5% (w/v) solution of copolymer in acetone and air drying. Alternatively, optimal surface concentration was obtained by continuous passage of Celgard sheet through a bath of 2% (w/v) copolymer in acetone at a rate of 100 ft/min, followed by passage through a heated drying chamber.

Solvents suitable for coating metal surfaces include, without limitation, methyl-ethyl-ketone (MEK), mixture of methylene chloride and alcohol (e.g., isopropyl and ethanol), toluene, acetone, trichloroethylene, cyclohexanone, and tetrahydrofuran. A suitable solvent should be able to dissolve the LSL copolymer and be able to wet the metal surface. In general, solvents having a solubility parameter of about 8 to 10 $(cal/min)^{1/2}$ should dissolve the LSL copolymer. See, e.g., Hoy, K. L. (1970) *J. Paint Technology* 42(541) :761–818. A further requirement for coating polymers and polymer-coated metals is that the solvent should not etch or degrade the polymer surface being coated. For example, additional suitable coating solvents include dibasic acid esters such as diisobutyl glutarate, glycol ethers, such as dipropylene glycol methyl ether, propylene glycol methyl ether (1-methoxy-2-propanol) and tripropylene glycol monomethyl ether, N-methyl pyrrolidone and the like. When using mixtures of methylene chloride in alcohol, the methylene chloride concentration is preferably at least 10% (v/v). Optimal surface concentrations of SMA-423 have been obtained by dipping stainless steel discs (316L stainless steel) in 1.0% and 2.0% (w/w) solutions of copolymer in MEK and air drying.

Relative surface concentration of the LSL copolymer can be quantitatively assessed by X-ray fluorescence (XRF). Silicon has a characteristic X-ray fluorescence band ($K\alpha$), the intensity of which is a function of the concentration of silicon atoms of the coated surface. By comparing the X-ray fluorescence intensity of the sample with an internal standard an intensity ratio can be calculated, which is a measure of the relative silicon surface concentration and therefore of the LSL surface concentration.

To carry out XRF analysis, the film or membrane sample to be measured is stretched over an X-ray sample cup (Chemplex #1930 sample cup) and held in place with a snap ring. A coated metal disc or coated polymeric article is placed directly in the sample compartment. The sample compartment of a Philips AXS Wave Length Dispersive Spectrometer is flushed with helium. The spectrometer should be fitted with a chromium X-ray tube. Other machine parameters are listed below.

| XRF MACHINE PARAMETERS | | | |
|---|---|---|---|
| Beam Filter | out | KV Setting | 60 |
| Collimator | coarse | MA Setting | 50 |
| Scintillator Detector | disable | PHS Baseline | 10 |
| Flow Counter | enable | PHS Window | 25 |
| Crystal | WC | Peak 2 Theta | 16.26° |
| Order | first | Peak Time | 120 sec |

When the silicon atoms in the triblock copolymer, for example, SMA423, are excited by the radiation coming from the chromium X-ray tube they emit a fluorescent radiation that is characteristic of Silicon ($K\alpha$). The intensity of this fluorescent radiation is directly proportional to the surface concentration of silicon and therefore to the concentration of SMA423. The intensity of the radiation is measured in terms of counts per second and normalized to an internal machine silicon standard which accounts for any possible variation in machine parameters. The internal machine standard used in these analyses provides a count rate of 42,000 counts/sec. This ratio is known as the Intensity Ratio which, again, is directly proportional to the surface concentration of the silicon. As previously noted, membrane dip-coated in a 0.5% copolymer solution had optimal biocompatibility. The Intensity Ratios measured on samples of such membranes were as follows:

| Sample No. | Intensity Ratio |
|---|---|
| 1 | 0.1836 |
| 2 | 0.1720 |
| 3 | 0.1699 |
| 4 | 0.1760 |
| 5 | 0.1725 |
| 6 | 0.1789 |
| 7 | 0.1897 |
| 8 | 0.1855 |
| 9 | 0.1793 |
| 10 | 0.1786 ± 0.0067 |
| (mean ± std. deviation) | |

From these and similar studies it has been determined that polymers (including membranes) and metal surfaces having copolymer coatings whose surface concentrations display XRF intensity ratios in the range 0.02–0.35 provide operable biocompatibility. A preferred range of XRF intensity ratios is from 0.05–0.25, while maximal biocompatibility with the membranes tested herein was observed with membranes having XRF intensity ratios in the range 0.16–0.2. It will be understood that those of ordinary skill in the art can measure optimally biocompatible surface concentrations of coatings according to the invention by using the XRF technique just described.

The coatings applied to porous membranes do not reduce or modify their porosity. For example, an optimally coated Celgard membrane and an uncoated membrane were tested for resistance to air flow according to the ASTM-D-726(B) test method. The manufacture's specification for uncoated Celgard membranes is 50–120 Gurley sec. A test sample, uncoated, had an air resistance of 74 Gurley sec., while the coated material had a resistance of 67 Gurley sec.

As previously noted, stainless steel disc dip-coated in 1.0% and 2.0% copolymer solution had optimal biocompatibility. The Intensity Ratios measured on samples of 316L stainless steel discs were as follows:

| Disc No. | SMA Solution Conc. (w/w) | Intensity Ratio |
| --- | --- | --- |
| 14 | 0.5 | 0.0785 |
| 21 | 1.0 | 0.0942 |
| 22 | 2.0 | 0.1482 |
| 23 | 3.0 | 0.1767 |
| 24 | 4.0 | 0.2106 |

Stainless steel surfaces having copolymer coatings whose surface concentrations display XRF intensity ratios in the range of 0.02 to 0.35 provide operable biocompatibility. A preferred range of XRF intensity ratios for stainless steel coatings is from 0.05–0.25, while maximal biocompatibility with the stainless steel discs tested herein was observed with discs having XRF intensity ratios in the range of 0.09–0.18. Excellent results have been obtained using 2.5% (w/w) SMA-423 for membrane coating and 1.0% (w/w) SMA-423 for stainless steel heat exchanger coating.

Biocompatibility involves various aspects of reactions between biological tissue and synthetic materials. The most common and dangerous for the patient are activation of the blood clotting cascade, complement activation, inflammatory cellular responses and platelet activation. Activation of the clotting reactions was measured either by a commercially-available thrombin-anti-thrombin ELISA test (Behring Diagnostica, Inc. Marburg, Germany) or by assaying kallikrein-like activity (intrinsic coagulation cascade) using a chromogenic substrate reaction available from Kabi Diagnostica, Molndal, Sweden. Complement activation was measured by an ELISA assay for soluble terminal complement complex (TCC) [Deppisch, R. et al. (1990) Kidney International 37:696–706]. Interleukin-1β(IL-1β) generation by mononucleocytes exposed to flat sheets or membranes is measured by an ELISA test available from R&D Systems Minneapolis, Minn. In addition, platelet adherence and activation onto test surfaces exposed to an ex vivo shunt was examined by scanning electron microscopy. An in vitro platelet activation test was also carried out.

It will be recognized that conventional polymeric stock, tubing, shaped articles and the like can also be coated by an LSL copolymer in the manner described for microporous membranes. Similarly, various metallic surfaces and articles can be coated by an LSL copolymer in the manner described for stainless steel discs. Surface concentration of LSL can be assessed by XRF in the same manner with optimal surface coating being within the same ranges of intensity ratios as for the exemplified polymeric membranes and metallic discs. Biocompatibility tests have also been carried out with sheets and tubing of polypropylene and polyvinyl chloride.

It has been discovered that effective LSL copolymer coating can be achieved on blood-contacting surfaces of an assembled oxygenator heat exchanger or to sub-assembled components of an oxygenator, thereby eliminating the need to use pre-coated membranes or pre-coated heat exchangers. By applying the coating at a post-assembly stage, the cost of manufacture is reduced, coated material is not wasted and the risk of damage to the coated surface is minimized. The post-assembly coating process carried out by pumping a solution of LSL copolymer of specified concentration at a predetermined flow rate through the blood-contacting channels of an assembled oxygenator heat exchanger, or through sub-assembled components of an oxygenator, such as through the oxygen-exchange and heat-exchange components separately.

Described herein are specific methods used to separately coat an oxygen-exchanger and a heat exchanger, using a recirculating system for pumping LSL copolymer solutions and for flushing out residual solvent with a flow of gas. Surprisingly, it was found that an SMA solution in MEK does not pass through an oxygenator membrane, from the blood side to the gas side, especially if the gas side ports are plugged while copolymer solution is flowing through the blood-coated side of the device.

A coating machine is used to coat the oxygen exchangers of oxygenators with LSL copolymer prior to heat exchanger attachment. The equipment coats the blood side of leak-tested oxygenator with SMA-423 using MEK as the solvent/carrier. During the coating operation, the gas-side of the oxygenator is completely plugged-off to help prevent MEK from flowing across the membrane into the gas-side of the device. Pneumatically actuated cylinders are used to plug-off the gas-side openings.

The coating machine contains one oxygen exchanger coating station. After an operator places the exchanger in a locating nest, the machine pumps an SMA/MEK solution (2.5% w/w) from a tank through the blood side of the oxygenator and back to the tank for a period of time sufficient to ensure contact with all surfaces. A flow switch downstream of the oxygenator detects that the specified flowrate has been achieved, typically about 1 gal/min. Compressed air, which has been dried and filtered, is then forced through the coated oxygenator for a period of time to flush and dry it of the solvent, usually about 10–14 30 minutes depending on air temperature. Complete solvent removal can be determined by drying the device to constant weight.

A filtered recirculation loop through the solvent tank is normally active. To coat an oxygenator, the SMA/MEK solution is diverted through a set of valves to the oxygenator. Solution then passes through a strainer and a flow switch and back to the tank. The coated oxygenator is then dried by routing air through a set of valves to the oxygenator and into a liquid/vapor separator. Liquid is recovered and routed back to the tank. Air and vapor are vented. Wetted materials will consist of stainless steel, teflon, polypropylene, ethylene-propylene, and silicone.

Three sample coating runs were conducted using different concentrations of SMA-423 in MEK, a flow rate of 4 1/min and contact time of one minute. The resulting surface concentrations of SMA on the membrane surface as measured by x-ray fluorescence (XRF) are shown in the following table.

| Run | SMA Concentration (% w/w) in MEK | XRF Analysis (Si Ratio Intensity) |
| --- | --- | --- |
| 1 | 1.0 | 0.0625 |
| 2 | 2.5 | 0.1768 |
| 3 | 4.0 | 0.3027 |

A Flat Sheet Heat Exchanger Coating Machine is used to coat heat exchangers with LSL copolymer. The equipment coats the blood side of leak-tested flat sheet heat exchangers with SMA-423 using MEK as the solvent/carrier at 1% (w/w).

The machine contains three heat exchanger coating stations. After an operator places a heat exchanger on the locating pins of one of the stations, the machine pumps an SMA/MEK solution from a tank through the blood side of the heat exchanger and back to the tank for a specified period of time sufficient to ensure complete surface contact, typically 15–14 30 seconds. A flow switch downstream of the heat exchanger detects that the constant flowrate (1 gal/min) has been achieved. Compressed air, which has been dried and filtered, is then forced through the coated heat exchanger for a period of time, typically 2–4 minutes, to flush and dry it of the solvent.

A filtered recirculation loop through the tank is normally active. When a heat exchanger station is selected for coating, the SMA/MEK solution is diverted through a valve manifold to the station selected. Solution then passes through a strainer and a flow switch and back to the tank. The coated heat exchanger is then dried by routing air through a valve manifold to the station and into a liquid/vapor separator. Liquid is recovered and routed back to the tank. Air and vapor are vented. Wetted materials consist of stainless steel, teflon, polypropylene, ethylene-propylene, and silicone.

Biocompatibility is also affected by the stability of the coating in the presence of blood. In particular, a biocompatible coating should not leach away or dissolve in contact with blood. Tests were run on samples of Celgard membrane coated with a 0.5% dip coating of SMA-423. XRF intensity ratios of individual samples and controls were measured before and after a 6.5 hour incubation at 37° C. with bovine whole blood. There was no significant difference in the membrane intensity ratios before and after incubation. SMA coating on metals demonstrates similar stability.

It was discovered, quite unexpectedly, that LSL copolymer coatings can be stabilized on the surface by exposing them to ionizing radiation. For instance, if an article is solvent coated with SMA 423 and then exposed to another solvent for SMA 423, the SMA 423 coating can be completely dissolved off the surface. If, however, the coated article is exposed to ionizing radiation, examples of which could be x-rays, γ-rays or an electron beam, and then contacted with a solvent for SMA 423, only a fraction of the SMA 423 is dissolved off the surface. The remaining SMA 423, which is not dissolved off the surface, appears to be tenaciously adhered to the surface. Biosafety of an LSL-coated article is therefore enhanced by exposing a coated article to ionizing radiation, since the tendency for the coating to be removed is reduced. X-rays in the dose range 0.25 to 13.0 Mrad will result in stabilizing the coating on blood-contacting surfaces. An x-ray dose of 12 Mrad results in rendering at least 50% of SMA-423 resistant to an ethanol wash (Example 7).

EXAMPLE 1

Inertness of LSL-coated microporous membrane to clotting activation as measured by thrombin-antithrombin assay.

Thrombin, a serine protease, is the central bioregulatory enzyme in hemostasis [Fenton, J. W. (1986) *Ann. New York Acad. Sci.* 485:5–15]. Assessment of thrombin generation is essential in order to evaluate the extent of thrombosis or hemostasis. In blood, the thrombin activity is mainly regulated by the serine protease inhibitor antithrombin III, which forms a stable, catalytically inactive complex with thrombin. Since the level of thrombin-antithrombin III complex (TAT) in blood reflects the formation of thrombin, TAT concentration has been suggested as a sensitive parameter of coagulation activity during extracorporeal circulation [Deguchi, K. et al. (1991) *Am. J. Hematology* 38:86–89]. Celgard membranes dip-coated with 0.5% SMA-423 (optimal surface concentration by XRF) were compared with uncoated Celgard membrane, 2.5% SMA-423-coated Celgard membrane (surface concentration too high by XRF) and polystyrene membranes. Heparinized human whole blood was exposed to the test membranes for up to 45 minutes. Samples were withdrawn at intervals and assayed for TAT by a commercial ELISA test (Behring) according the instructions of the manufacturer. Results are shown in FIG. 1. The coated membranes showed significantly lower TAT than either the polystyrene positive control or uncoated Celgard membrane. In a separate experiment, blood samples containing varied heparin levels (3.0, 1.0 or 0.3 U/ml) were tested for TAT activation after 30 minute exposure to various test membranes, as above, in addition to Celgard membrane coated with an unfilled silicone (PS-252). The results are shown in FIG. 2. The 0.5% SMA-423-dipcoated membrane was markedly superior to other test membranes including the 2.5% SMA-423-coated membrane.

EXAMPLE 2

Biocompatibility of LSL-coated microporous membrane as measured by kallikrein-like activity (intrinsic clotting cascade), terminal complement complex (TCC) activity (complement activation) and interleukin-1β (IL-1β) mononucleocyte activation). To measure contact phase activation, we used a chromogenic substrate assay to monitor the generation of kallikrein-like activity in plasma was used. Unlike factor XIIa, almost all kallikrein is released from the surface into the fluid phase upon activation. The chromogenic substrate is commercially available, and testing protocols are well established [Lottenberg, R. et al. (1981) *Meth. Enzymol.* 80:341–361; Gallimore, M. J. et al. (1982) *Thromb. Res.* 25:29–298]. To measure complement activation, TCC was assayed, which was considered to be the best index of C5–C9 activation during cardiopulmonary bypass [Videm, V. et al. (1992) *Ann., Thorac. Surg.* 54:725–731]. In order to validate the results, other biomaterials with known strong or weak complement activating potential were included in the tests. It has been shown that the mononuclear cells (monocytes, lymphocytes) secrete IL-1β when exposed to bioincompatible materials. Therefore, IL-1β is another good index for biocompatibility [Cardona, M. A. et al. (1992) *J. Biomed. Mater. Res.* 6:851–859]. In this study, IL-1β production was measured on different materials including Cuprophan and AN69 dialysis membranes (two hydrophilic surfaces), and both untreated and SMA-coated Celgard polypropylene membranes (hydrophobic surfaces). Lipopolysaccharide (LPS), a potent inducer of IL-1β production, was used as a positive control (data not shown). Blood from three donors were used in this assay. It should be noted that mononuclear cells from different donors will react differently to different surfaces, resulting in large interdonor variation in results. Nevertheless, the coated and uncoated Celgard membrane samples show no difference in IL-1β released (Table 1). In comparison, both Celgard membrane and SMA-coated Celgard membrane induce significantly less IL-1β production than do the more hydrophilic Cuprophan and AN69 materials. As in Example 1, human whole blood was exposed for varying times to the described membranes. Kallikrein-like activity was measured using the chromogenic substrate S-2302 (Kabi), which yields p-nitroanaline upon enzymic hydrolysis, measurable by an absorbance change at 405nm. Soluble TCC was measured by an ELISA assay as described by Deppisch (1990). IL-1β was measured by an ELISA assay available commercially from R&D Systems. The results are given in Table 1.

The kallikrein-like activity test revealed that optimally-coated Celgard membrane was superior to either uncoated or too-heavily coated membrane. All three were superior to polystyrene.

The results of complement activation show that Celgard membranes are weak complement activators, whether coated or not. The extent of complement activation was comparable to a commercial polyacrylonitrile dialysis membrane, AN69, known to be a weak complement activating material. Cuprophane, another commercial dialysis membrane, showed the highest complement activation, consistent with the reports of others.

less advanced, showing only dendritic forms. Platelet density was always lower on the SMA-coated surfaces than the control surfaces. Results were even more dramatic in tests with non-heparinized animals, where control non-coated tubes became occluded with fibrin clots and trapped red cells.

EXAMPLE 4

Figure 3:
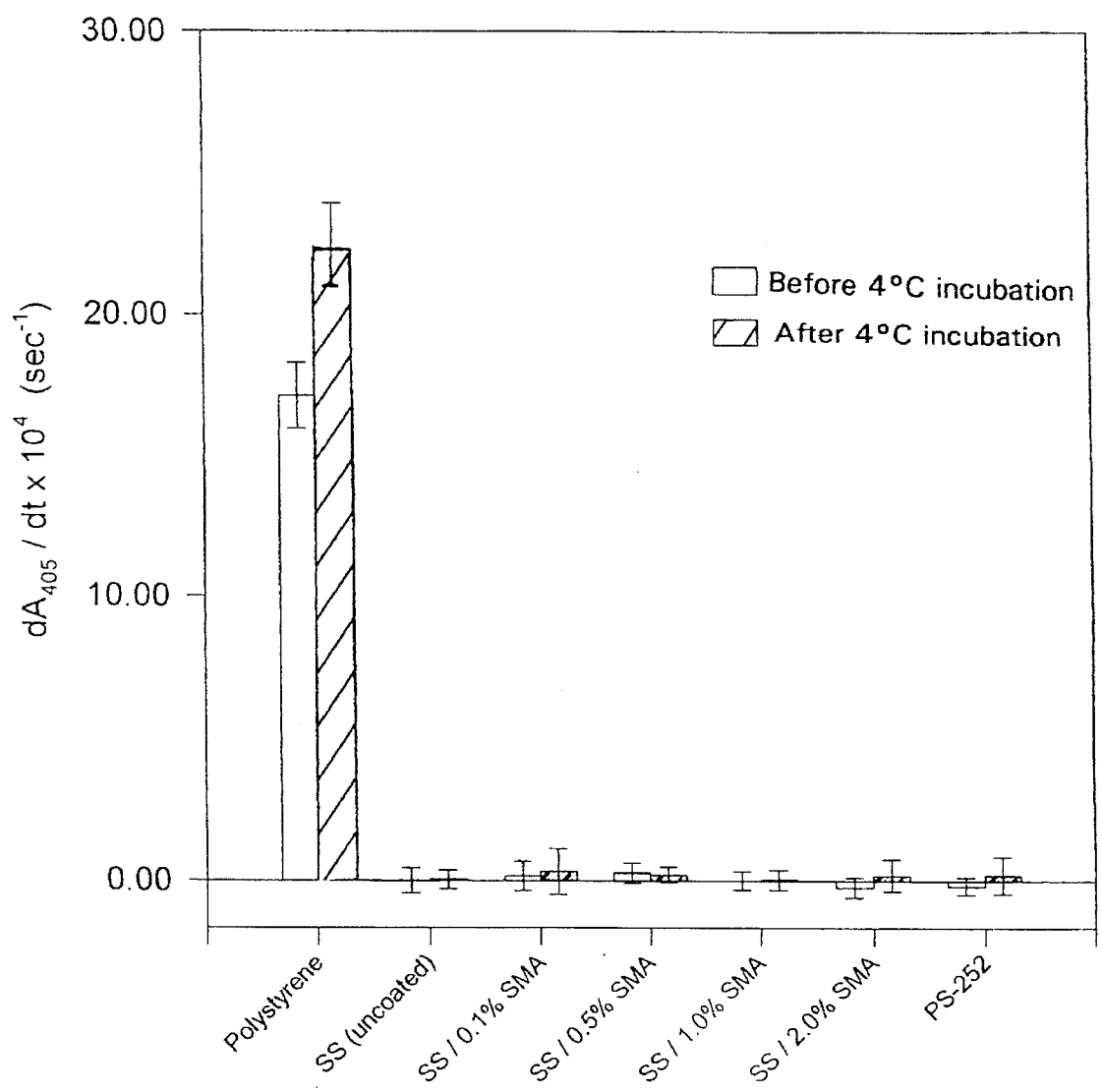
FIG. 3 is a graph of kallikrein-like activity in dilute platelet-poor plasma after 3 minute exposure at 4° C. to various surfaces.
Figure 4:
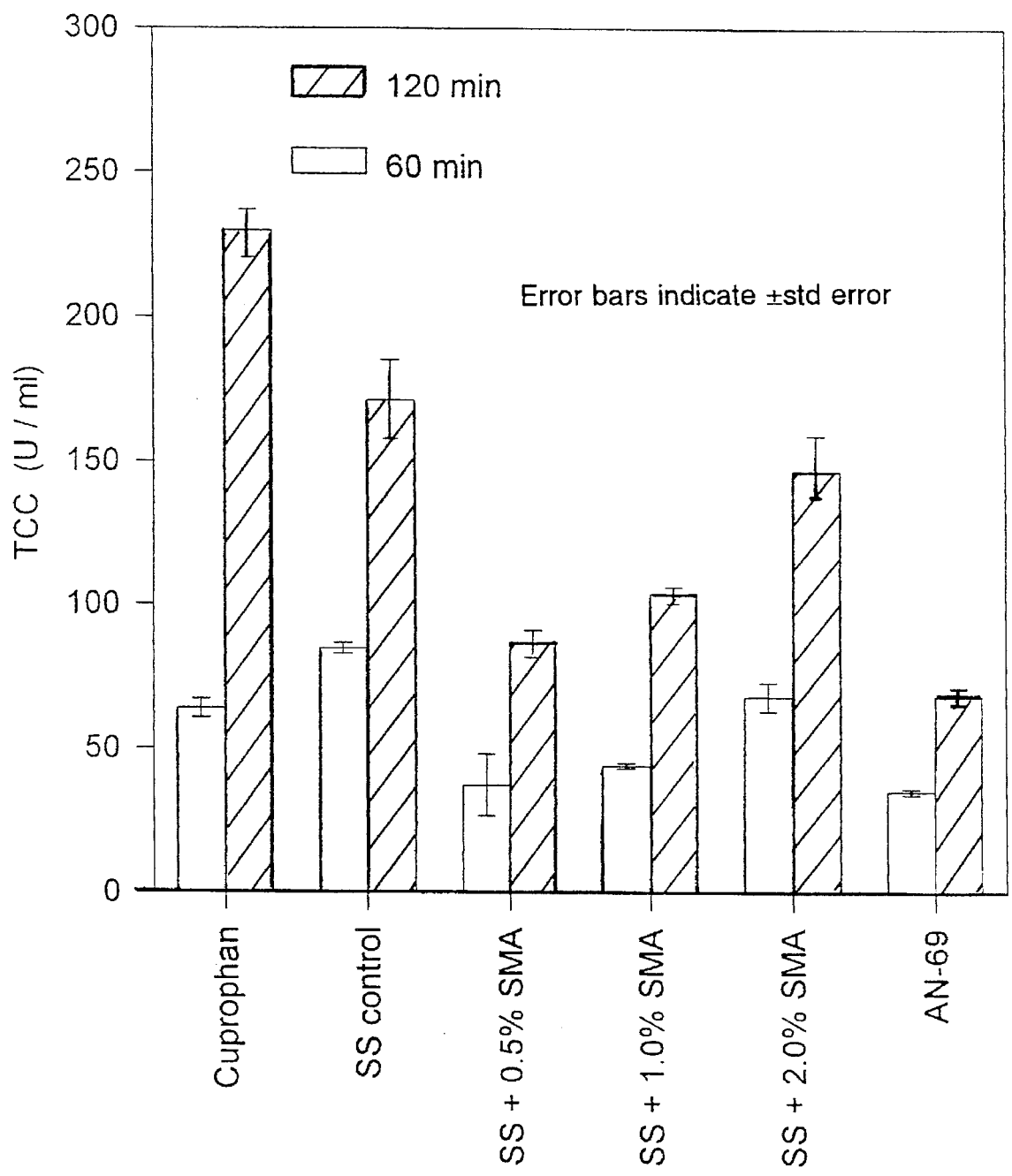
FIG. 4 is a bar graph showing the rate of the exponential increase of total complement complex in recalcified human whole blood after exposure to various surfaces.
Figure 5A:
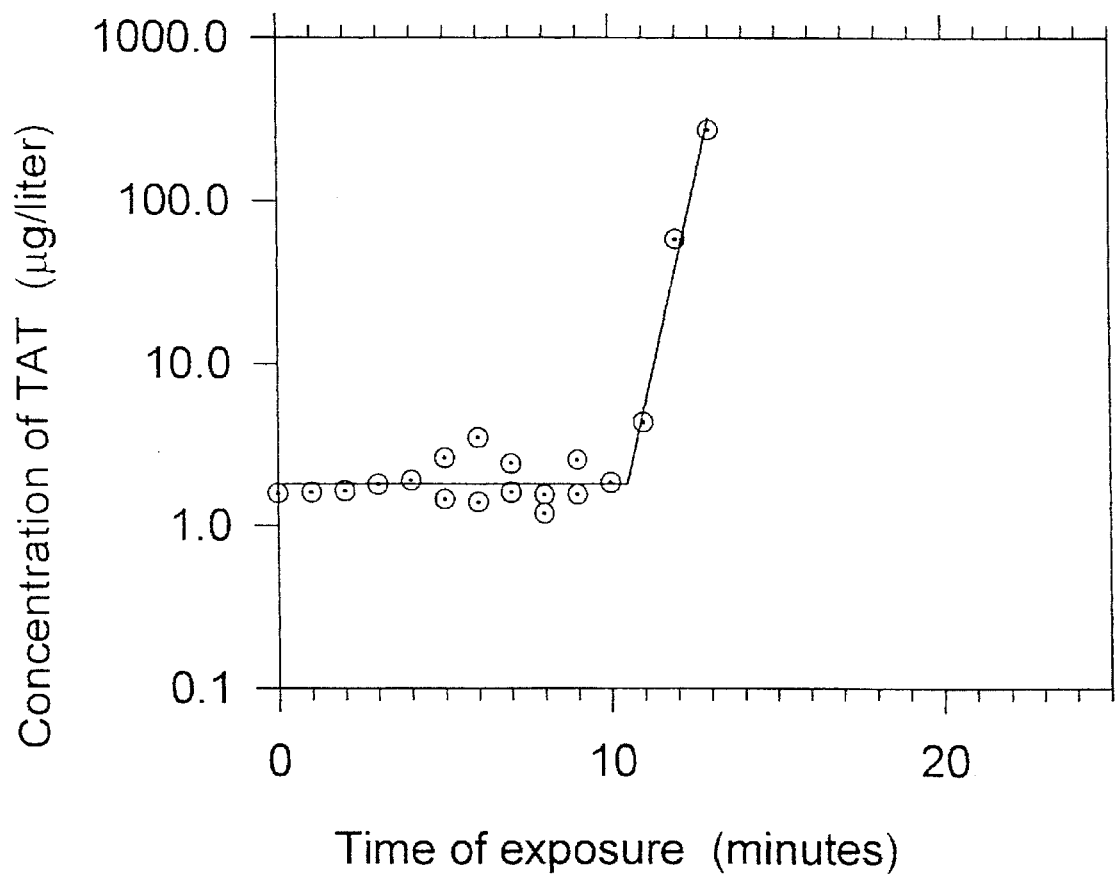
FIGS. 5A–5G are graphs of TAT complex in recalcified anticoagulated human whole blood exposed to various surfaces for times indicated on the abscissas.
Figure 5B:
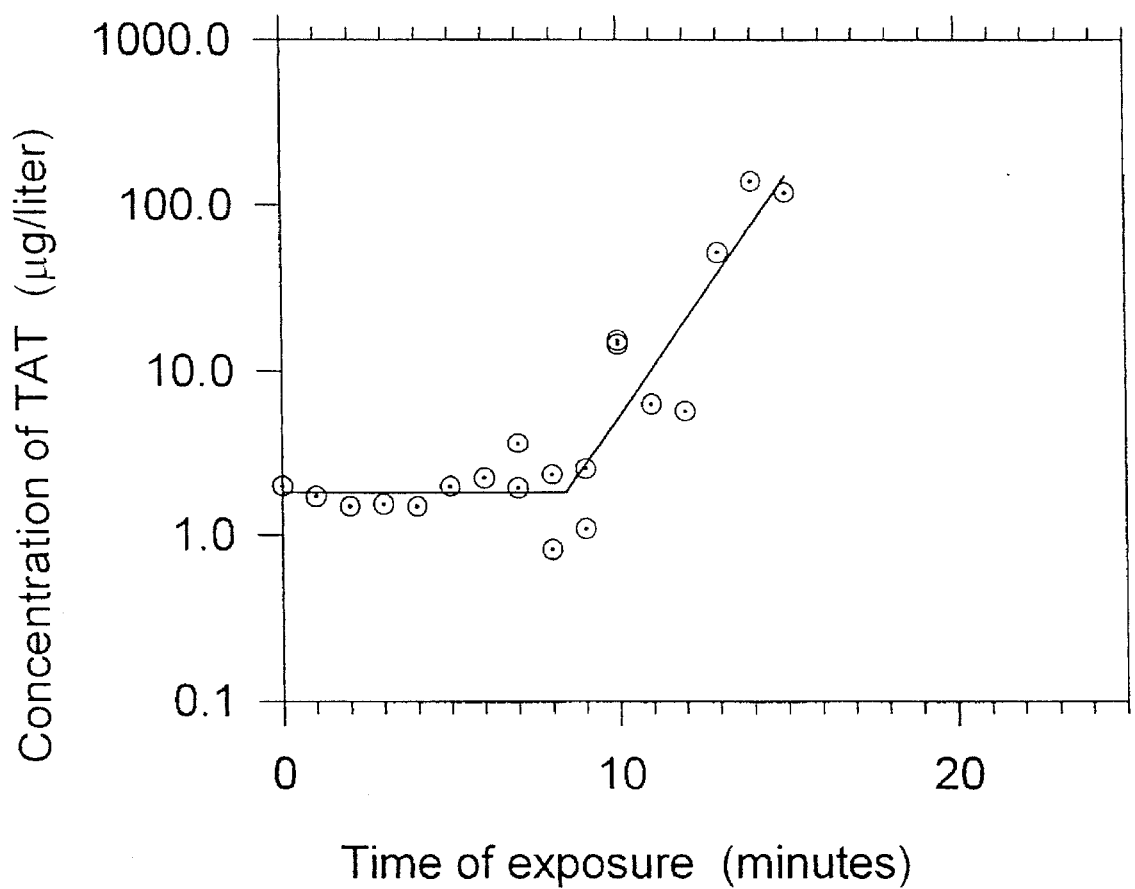
Figure 5C:
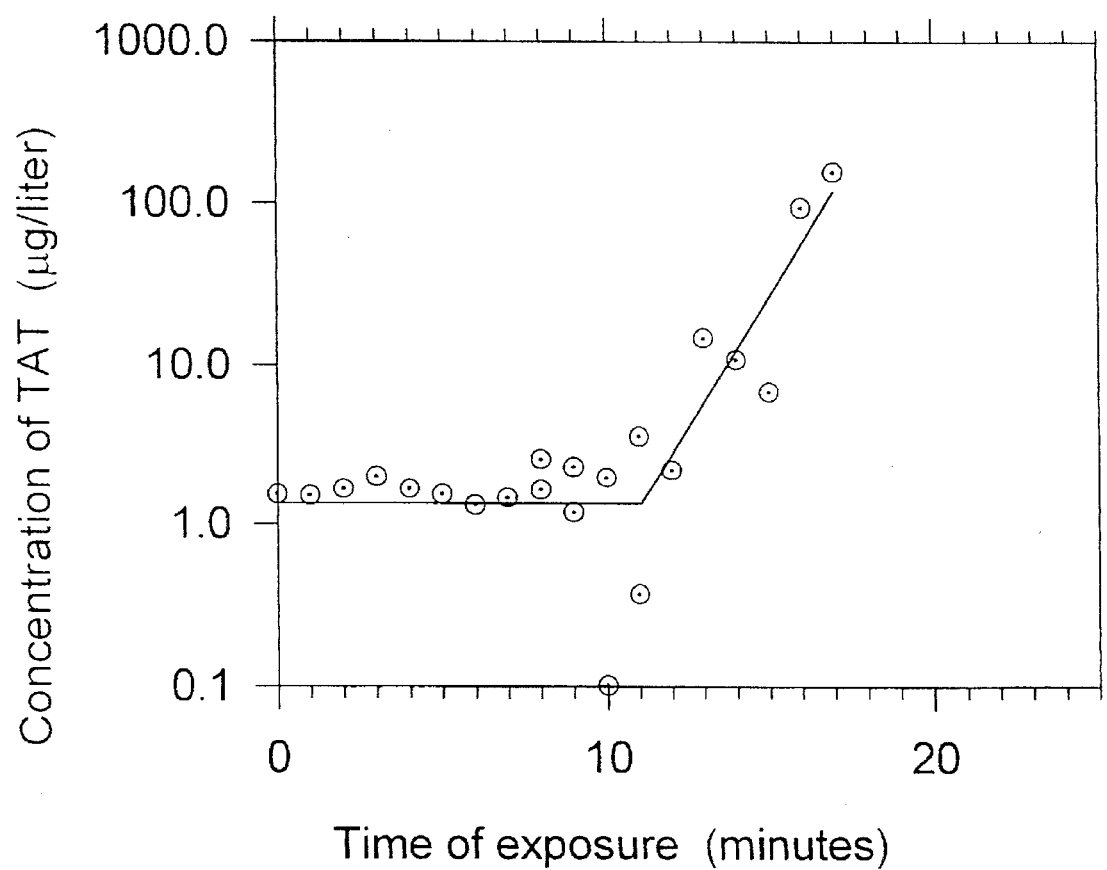
Figure 5D:
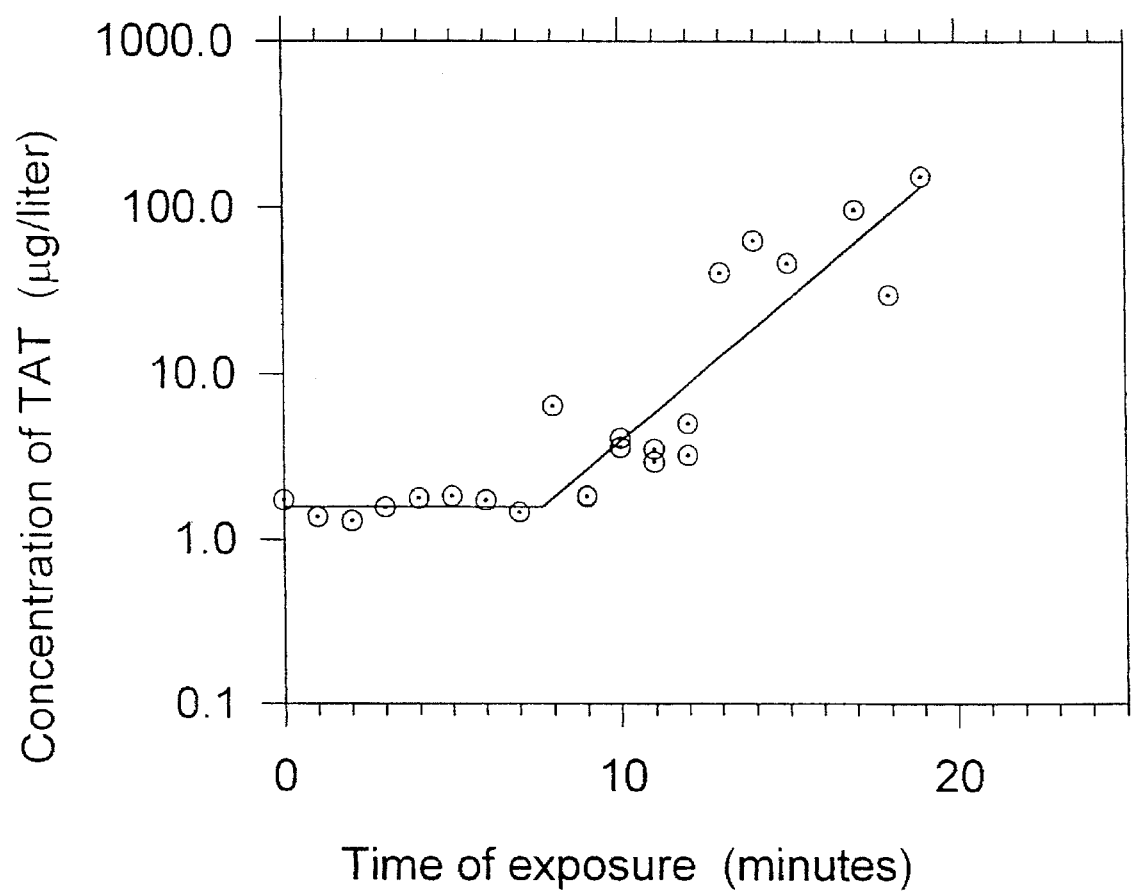
Figure 5E:
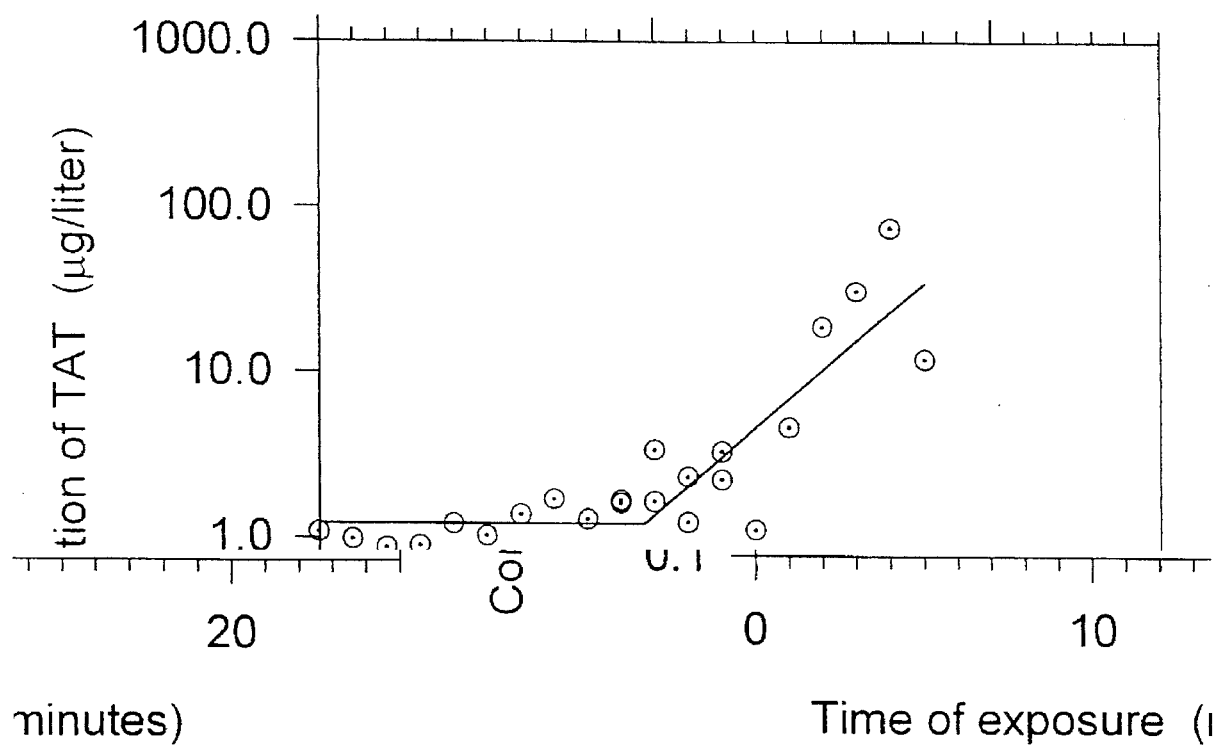

Biocompatibility of LSL-coated 316L stainless steel discs as measured by kallikrein-like activity (intrinsic clotting cascade) and terminal complement complex (TCC) activity (complement activation). 316L stainless steel discs dip-coated with varying concentrates of SMA-423 (0.1%, 0.5%, 1.0% and 2.0% solutions (w/w) in MEK were compared with uncoated 316L stainless steel disc, "wettable" polystyrene and PDMS (PS-252)-coated polystyrene (United Chemical Technology, Inc., Bristol, Pa.). Diluted platelet-poor plasma was exposed to the test surfaces for up to 10 minutes. Samples were withdrawn and assayed for kallikrein-like activity using the chromogenic substrate and testing protocol described in Example 2. Soluble TCC was measured by an ELISA assay as described by Deppisch (1990). The results are given in FIGS. 3 and 4.

The kallikrein-like activity test (FIG. 3) shows that 316L stainless steel discs are not contact activators of the intrinsic coagulation cascade, whether coated or not.

TABLE 1

Results of Biocompatibility Assays: Uncoated and SMA-Coated Celgard Membrane

| Material | Maximum KK-like Activity* (dA/dt × $10^{-4}$ min$^{-1}$) | TCC Activity** at 120 min exposure (Units/ml plasma) | IL-β(ng/ml) Donor 1 | Donor 2 | Donor 3 |
|---|---|---|---|---|---|
| Celgard - uncoated | 307 | 61.2 ± 4.3 | 4.2 | 6.8 | 6.0 |
| Celgard - 0.5% SMA-423 | 125 | 64.0 ± 1.8 | 7.6 | −0.5 | 6.2 |
| Celgard - 2.5% SMA-423 | 450 | 73.3 ± 4.1 | 0.0 | 7.2 | 10.8 |
| Polystyrene | 940 | — | — | — | — |
| AN69 | — | 61.0 ± 2.9 | −0.5 | 92.0 | 500 |
| Cuprophan | — | 531.3 ± 30.8 | 340 | 126 | 500 |

*The "kallikrein-like activity" in plasma samples is proportional to the rate of change of absorbance at 405 nm, the analytical wavelength used in this assay for measuring the generation of p-nitroanaline from the chromogenic substrate, S-2302
**TCC Activity values assume 1 Unit = 42 ng TCC
— Material not tested under this assay

EXAMPLE 3

Platelet adhesion and activation. Canine ex vivo arteriovenous shunts were used to study platelet adhesion and activation. Similar studies have been reported by Lelah, M. D. et al. (1984) *J. Biomed. Mater. Res.* 8:475–496, and by Zingg, W. et al. (1986) *Life Support Syst.* 4:221–229. SMA-treated polypropylene tubing was compared to uncoated tubing and uncoated polyvinyl chloride tubing. Animals were systemically heparinized to mimic extracorporeal circulation conditions. Shunts were removed at 30 minute and three hour intervals. Samples of control and coated tubing were fixed with 2% glutaraldehyde in saline and examined by scanning electron microscopy using a JEOL JSM-6400 instrument. Platelet deposition displayed two different patterns. On control surfaces, after 30 minutes exposure, platelets were uniformly distributed, of spherical or dendritic shape, attached to the surface in a single layer. At 3 hours, two layers were seen on control tubing. The initially deposited platelets progressed to the most activated pancake form and were covered by the second layer of fresh platelets with mostly dendritic form. In contrast, on the SMA-coated surfaces, only one platelet layer was seen and activation was The results of complement activation (FIG. 4) show that SMA coating reduces TCC levels over a wide range of coating solution concentration. Complement activation by 316L stainless steel coated with 0.5% SMA-423 approached that of a commercial polyacrylonitrile dialysis membrane, AN69, known to be a weak complement activating material.

EXAMPLE 5

Figure 8:
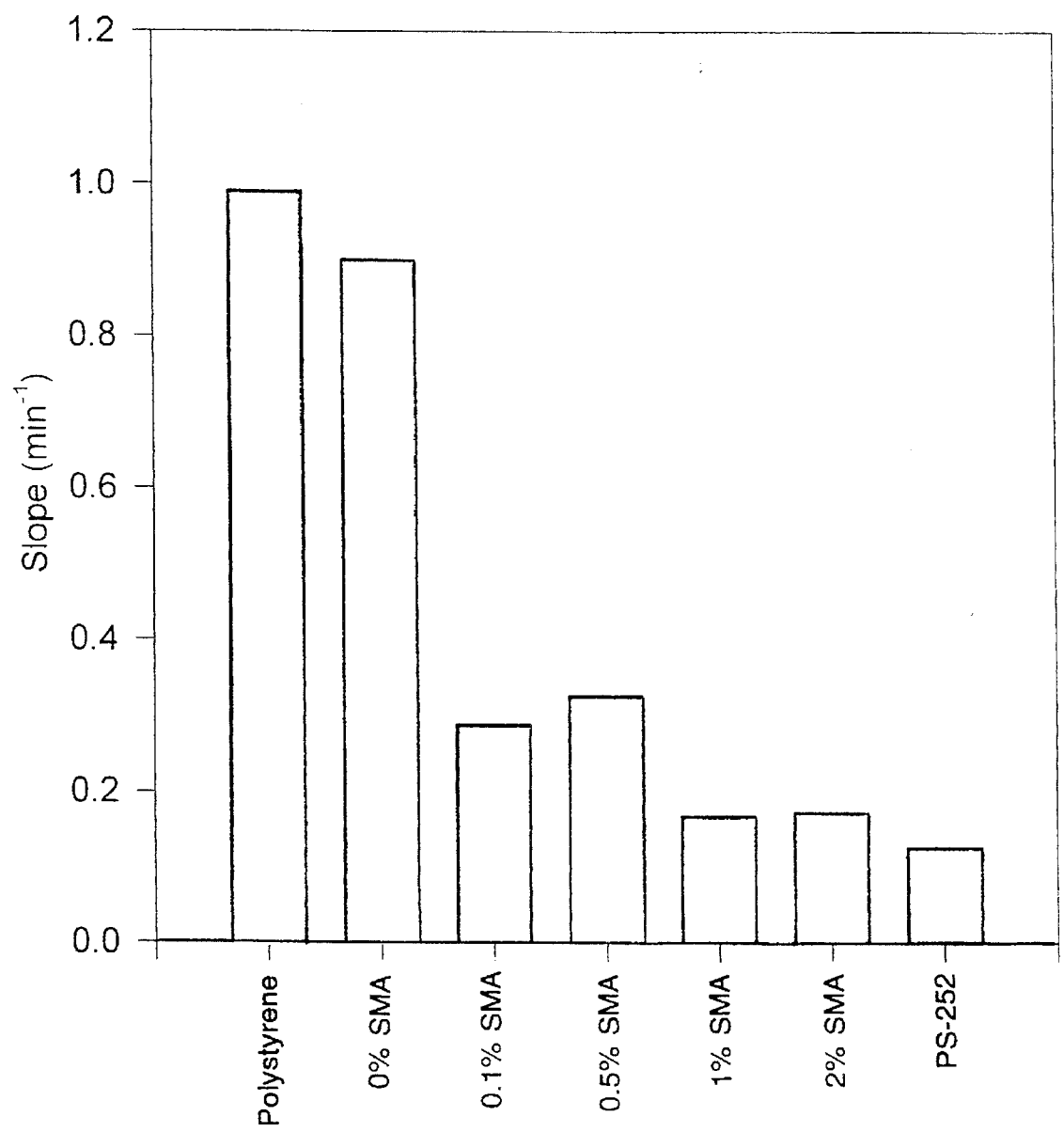
FIG. 8 is a bar graph showing the rate of the exponential increase of TAT complex in recalcified human whole blood after exposure to various surfaces.
Figure 2:
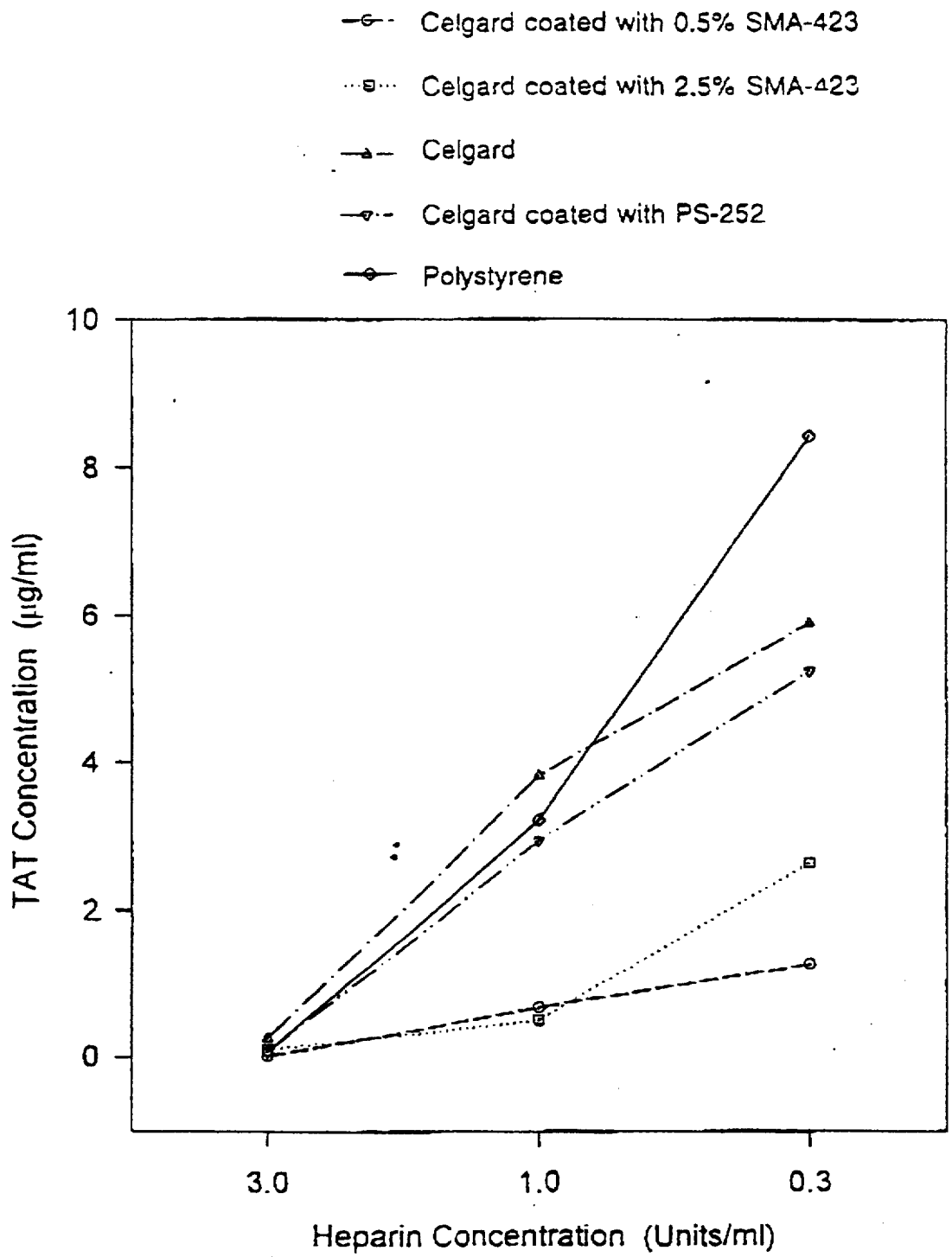
Figure 5E:
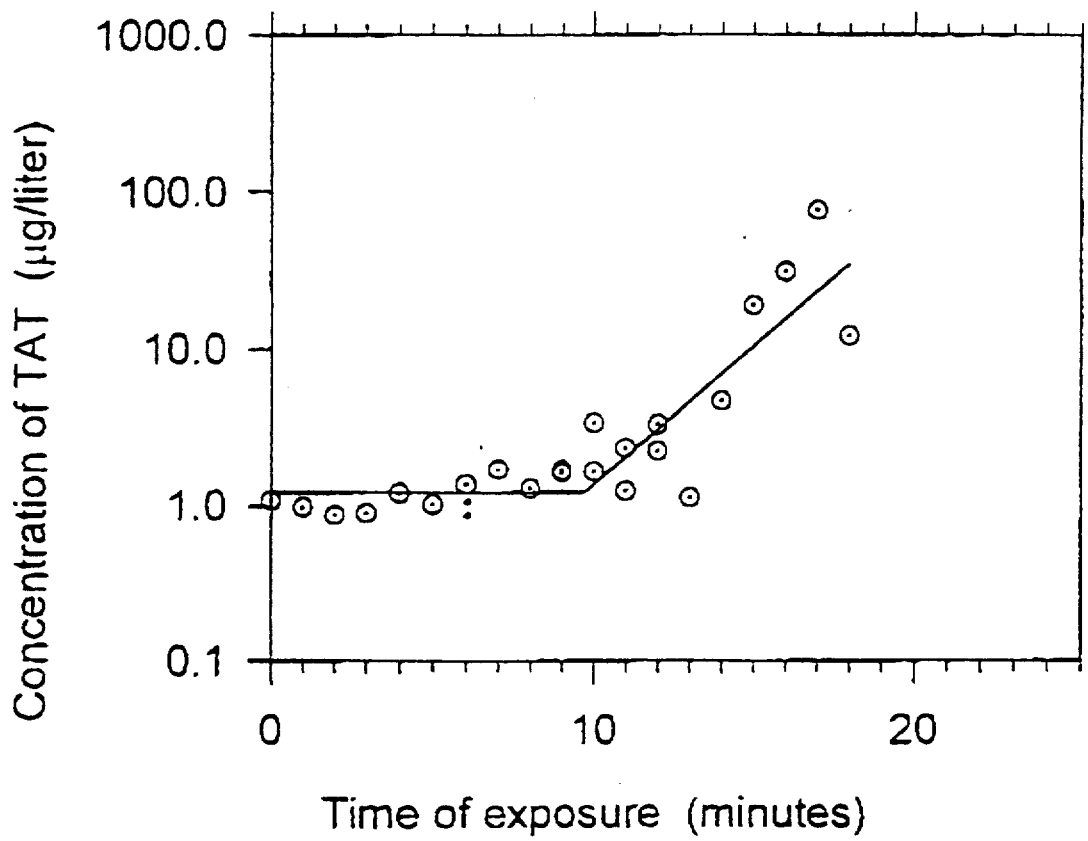
Figure 5F:
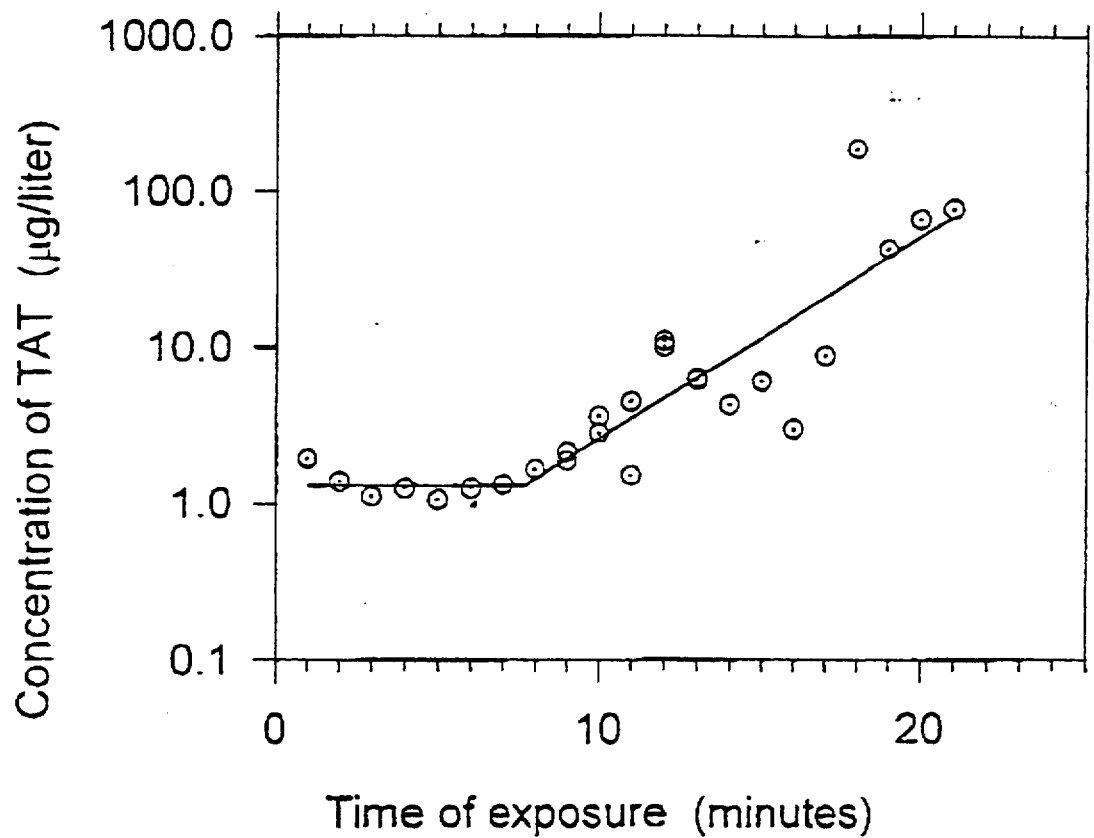

Biocompatibility of LSL-coated 316L stainless steel discs as measured by thrombin-antithrombin assay (TAT). Recalcified anticoagulated human whole blood was exposed to the test surfaces for up to 20 minutes. Samples were withdrawn at intervals and assayed for TAT by a commercial ELISA test, as previously described. Results are shown in FIGS. 5–8 and Table 2. As shown in FIG. 5, an initial lag period is typically followed by an exponential increase in the generation of TAT in recalcified human blood. The clotting time (FIG. 6), defined as the time at which the last sample is collected prior to clotting decreases with increasing surface thrombogenicity. The lag periods (FIG. 7) range from approximately 1 minute (for strongly contact-activating materials) to as much as 12 minutes for non-contactactivating materials). The rate of the exponential increase in TAT that follows a lag period increases with increasing surface thrombogenicity (FIG. 8).

used for experimentation that was performed in a 37° C. room.

TABLE 2

Platelet and Leukocyte Compatibility in vitro study

| | PLATELETS | | | NEUTROPHILS and MONOCYTES | LEUKOCYTES L-selectin |
|---|---|---|---|---|---|
| | Platelet Count % Resting WB | % Microparticles | % P-selectin Positive | CD11b Expression arbitrary fl units | Expression (% loss) |
| Resting WB | 100 | 13 ± 7 | 8 ± 4 | 100 | 0 |
| Silastic ™ | 80 ± 14 | 19 ± 2 | 7 ± 4 | 100 ± 0 | 7 ± 10 |
| Polyethylene | 53 ± 11 | 32 ± 9 | 11 ± 8 | 106 ± 10 | 19 ± 13 |
| PVC | 65 ± 7 | 27 ± 10 | 10 ± 7 | 101 ± 2 | 20 ± 12 |
| PVC compounded with SMA | 81 ± 6 | 19 ± 3 | 8 ± 3 | 106 ± 10 | 31 ± 12 |
| Polypropylene | 31 ± 4 | 45 ± 29 | 6 ± 3 | 100 ± 0 | 13 ± 19 |
| Polypropylene compounded with 1% SMA | 62 ± 7 | 31 ± 5 | 12 ± 9 | 126 ± 36 | 19 ± 9 |
| Polypropylene coated with 2.5% SMA | 69 ± 8 | 28 ± 9 | 11 ± 10 | 127 ± 23 | 31 ± |

Figure 6:
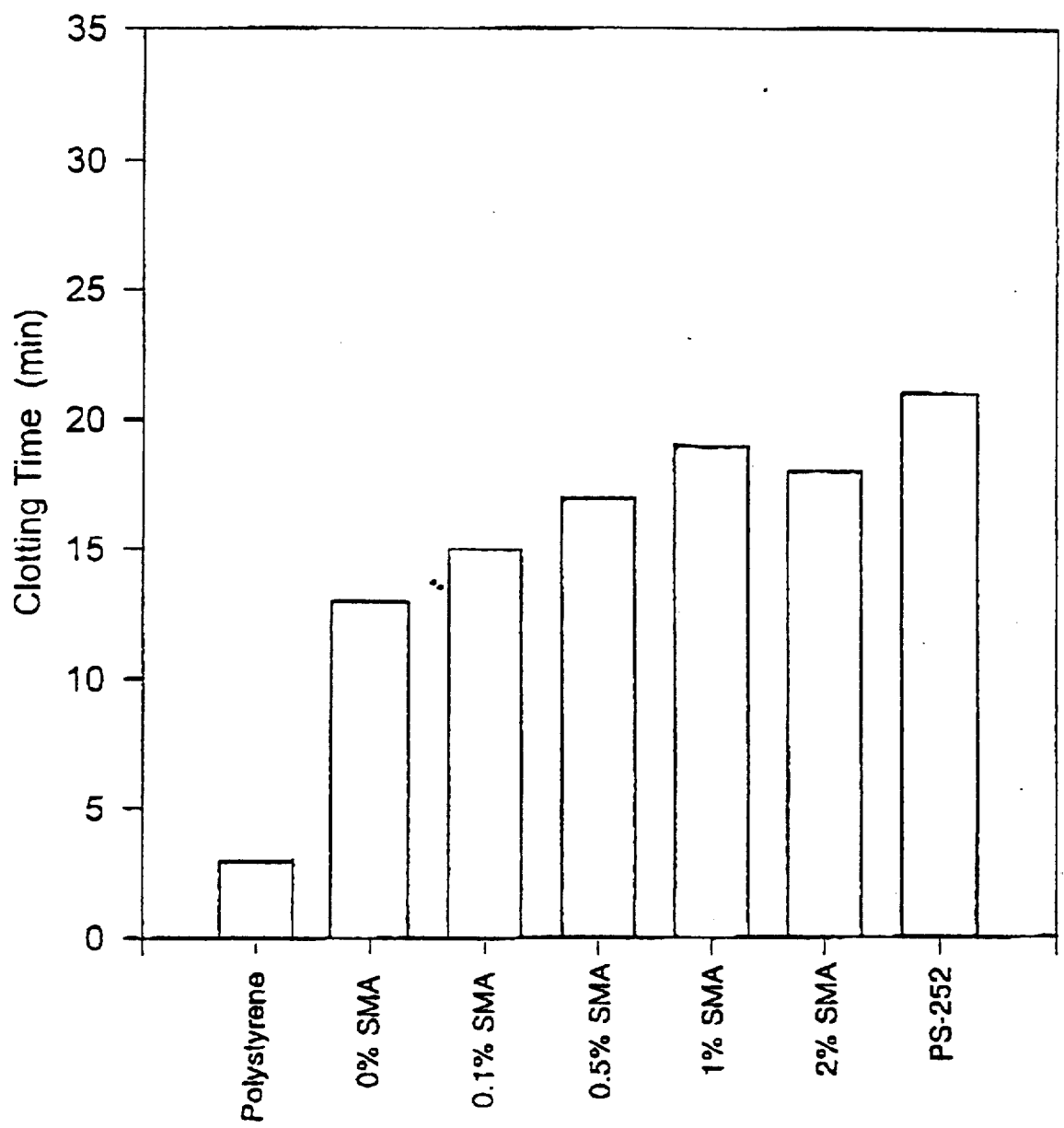
FIG. 6 is a bar graph of the clotting time of recalcified human whole blood exposed to various surfaces.
Figure 5G:
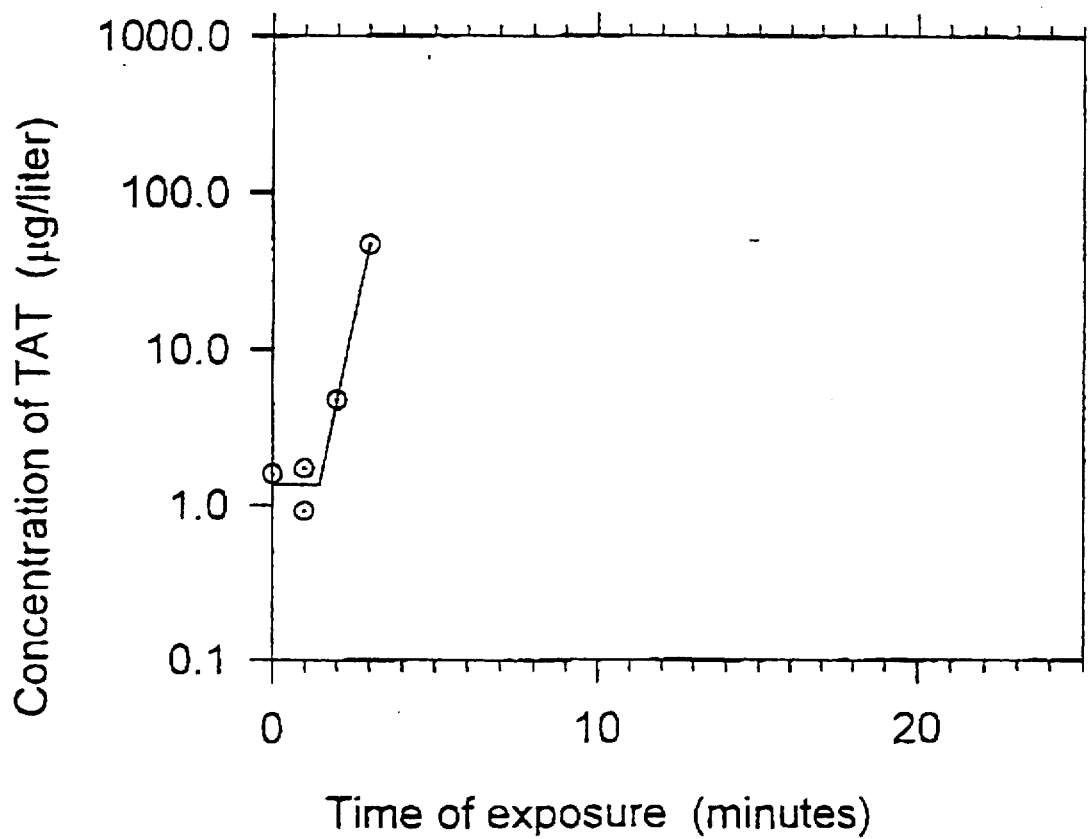
Figure 7:
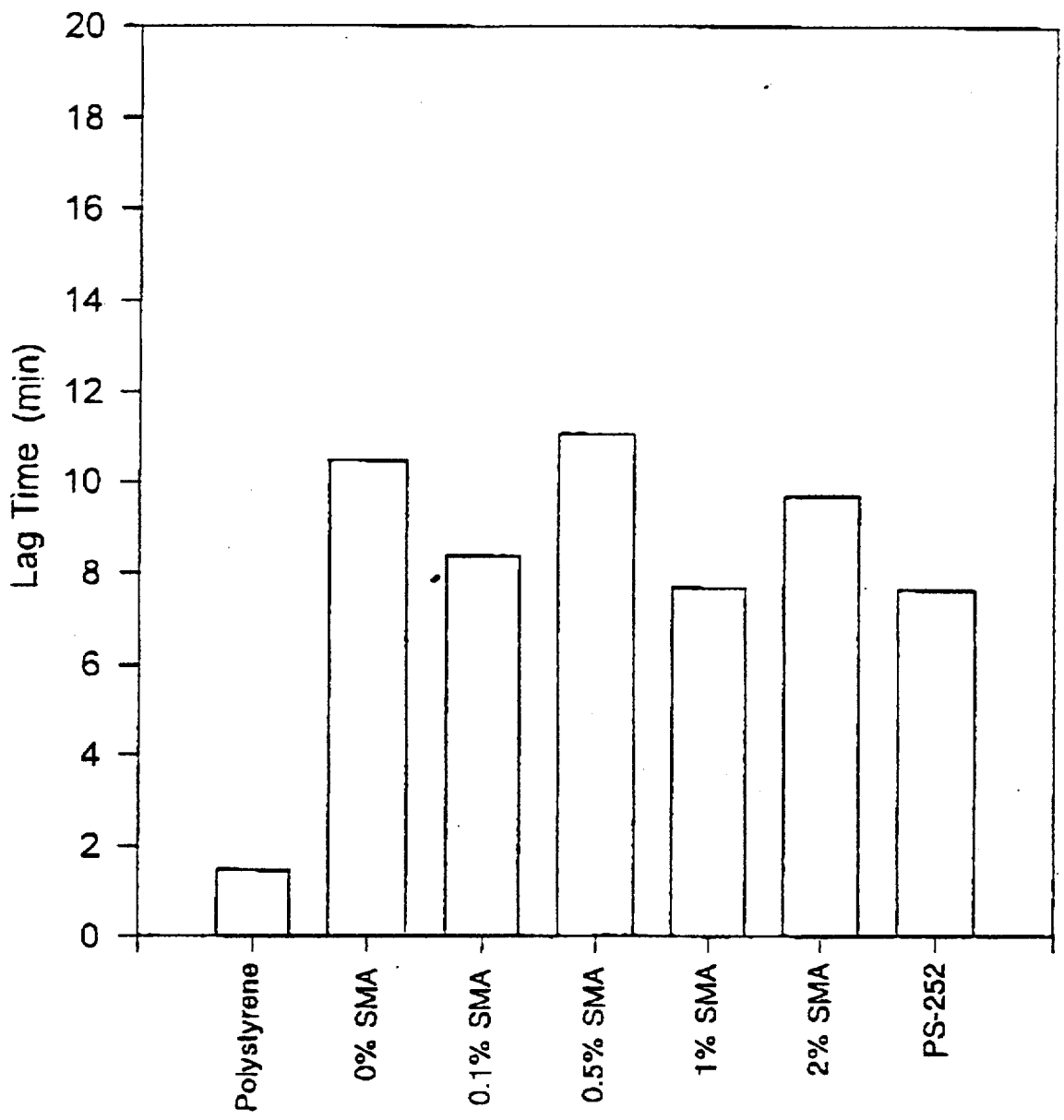
FIG. 7 is a bar graph of the TAT generation lag periods of recalcified human whole blood exposed to various surfaces.
Figure 1:
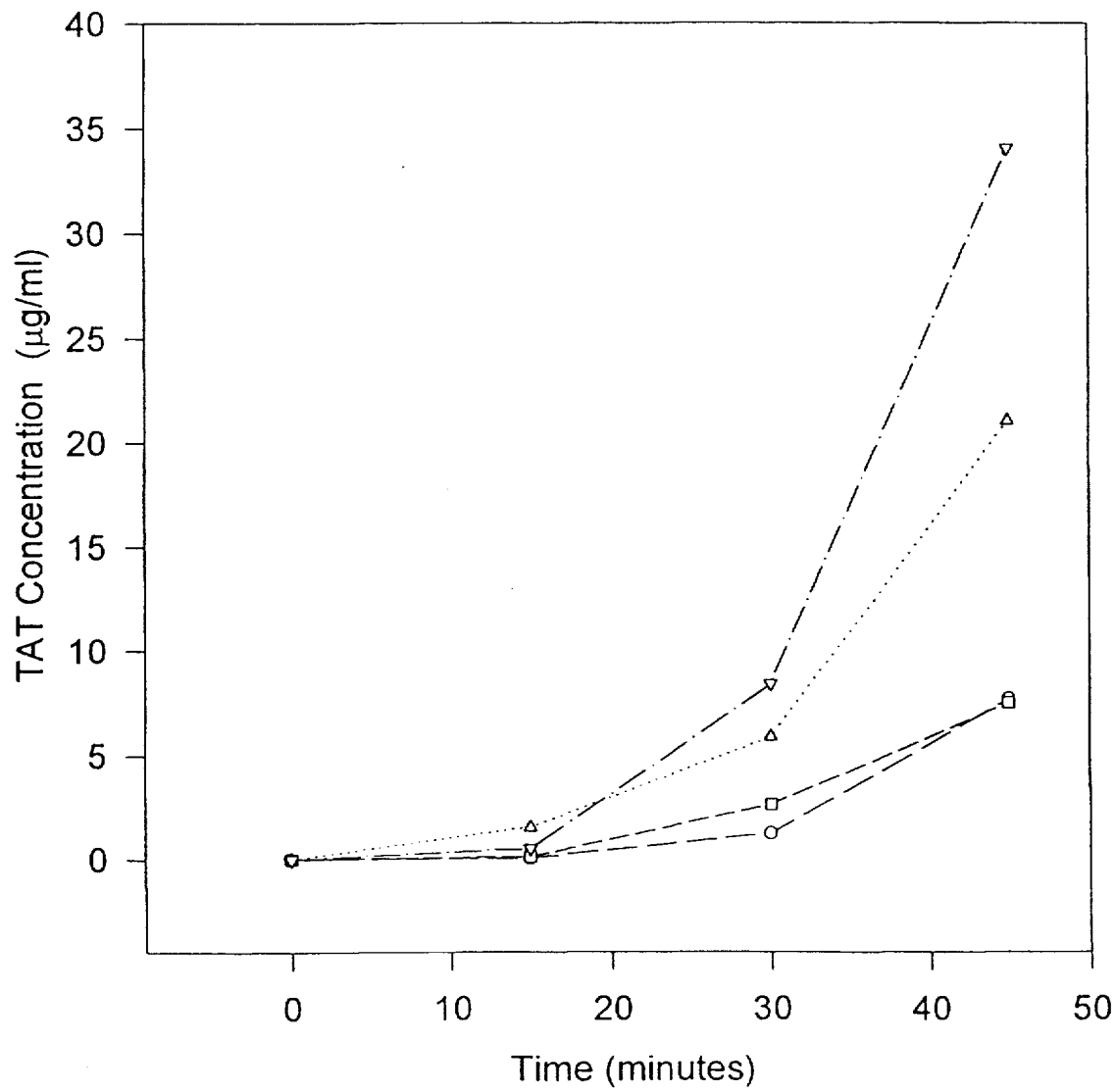
Figure 2:
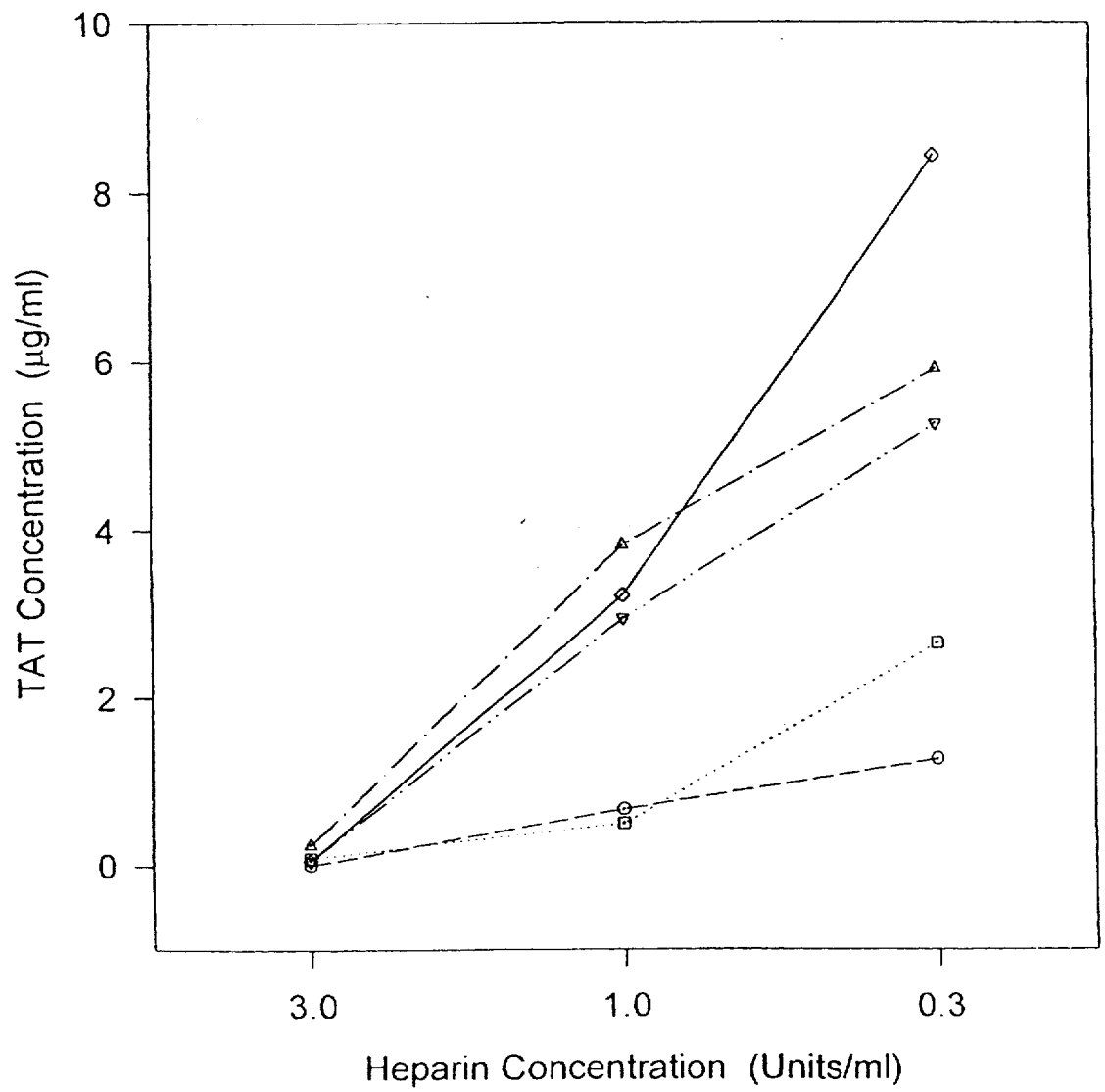
Figure 3:
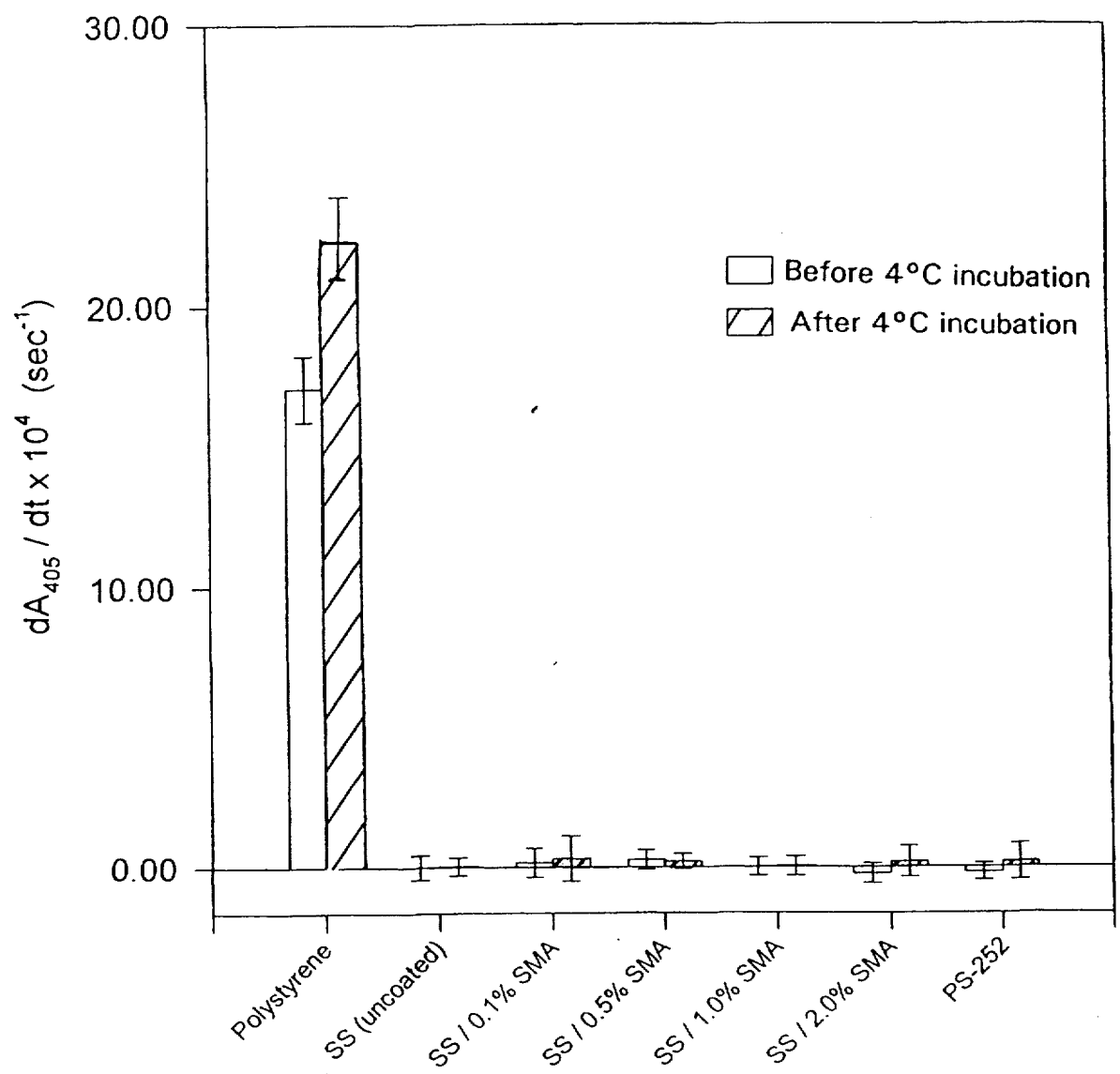
Figure 4:
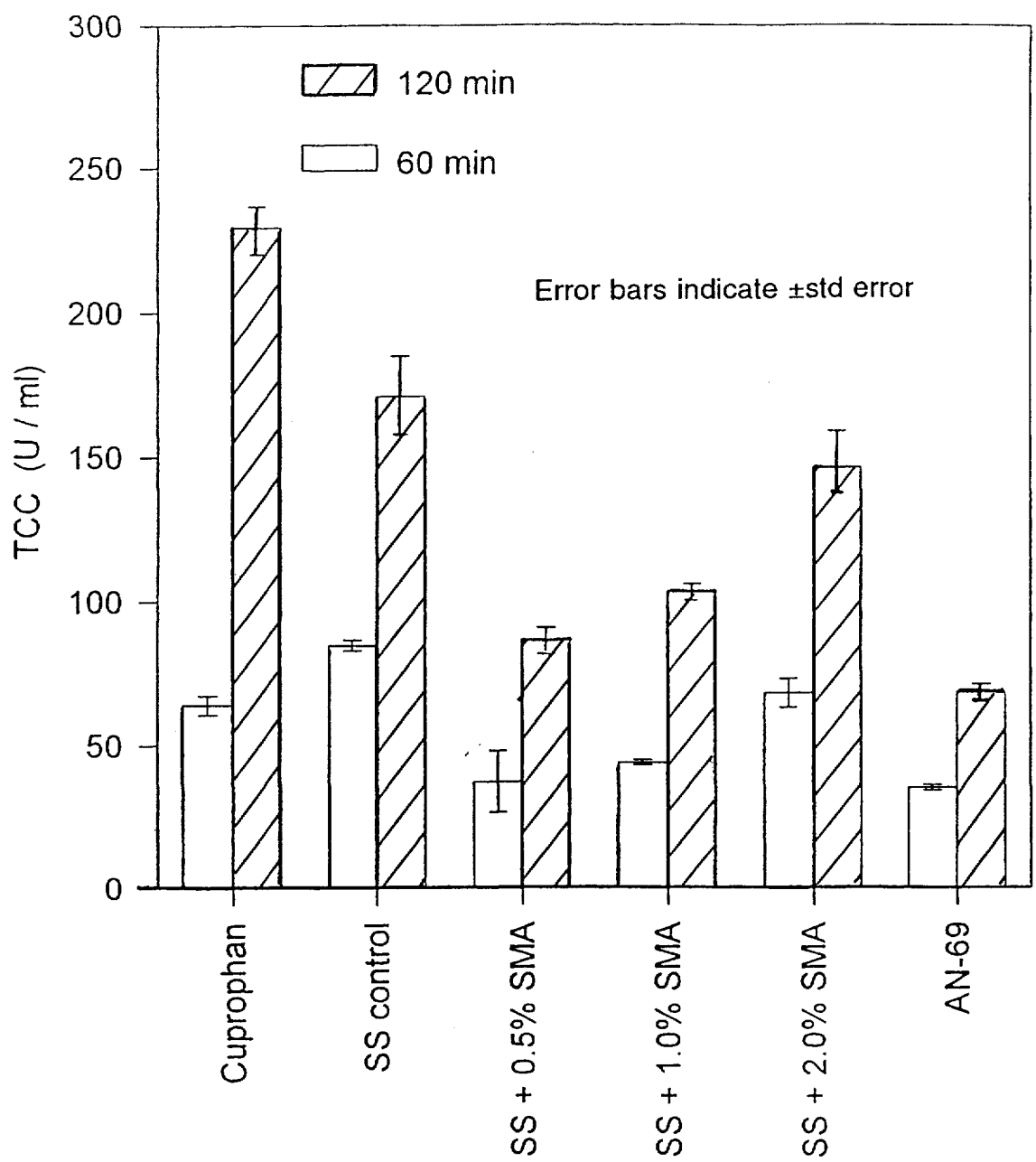
Figure 5A:
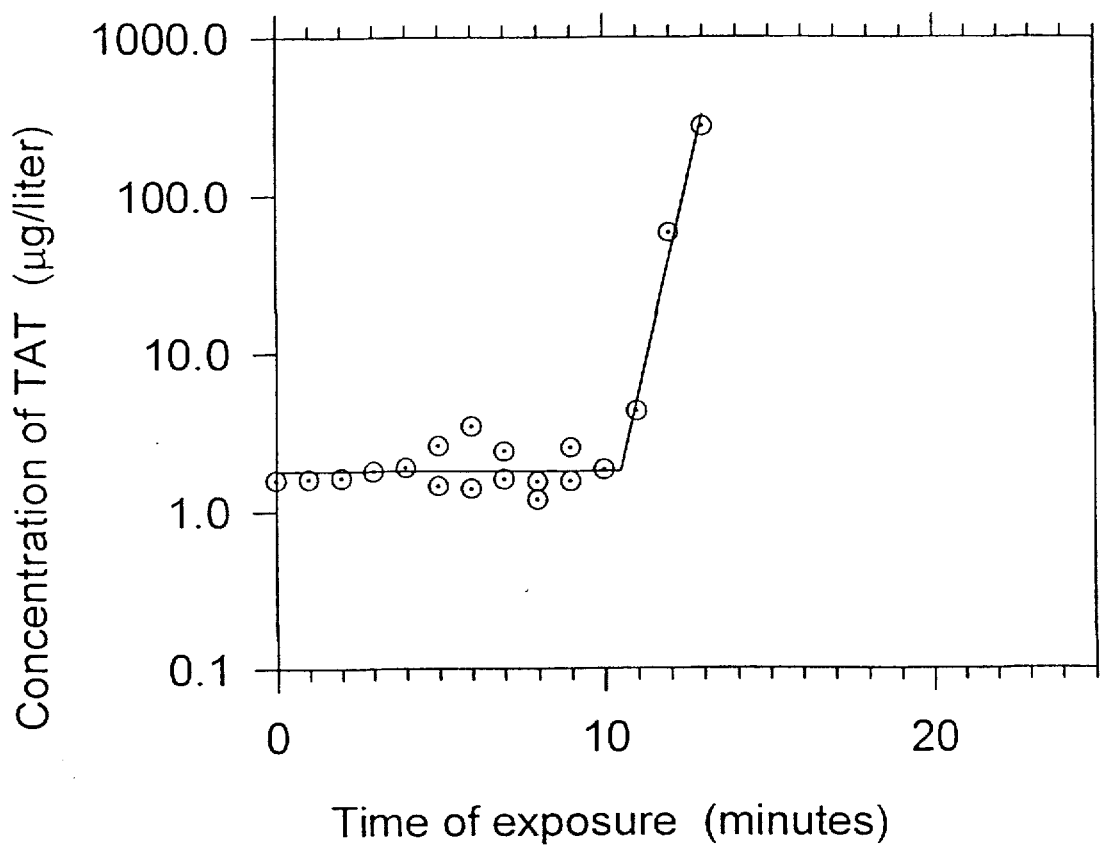
Figure 5B:
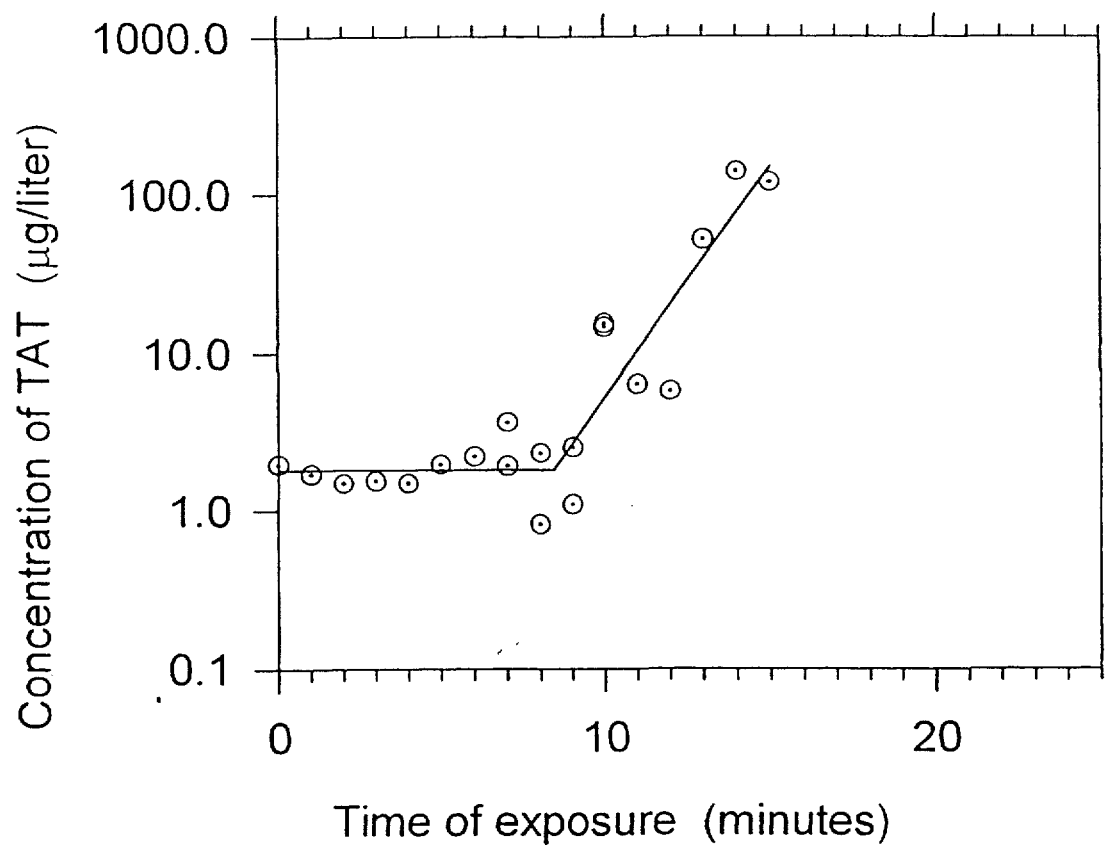
Figure 5C:
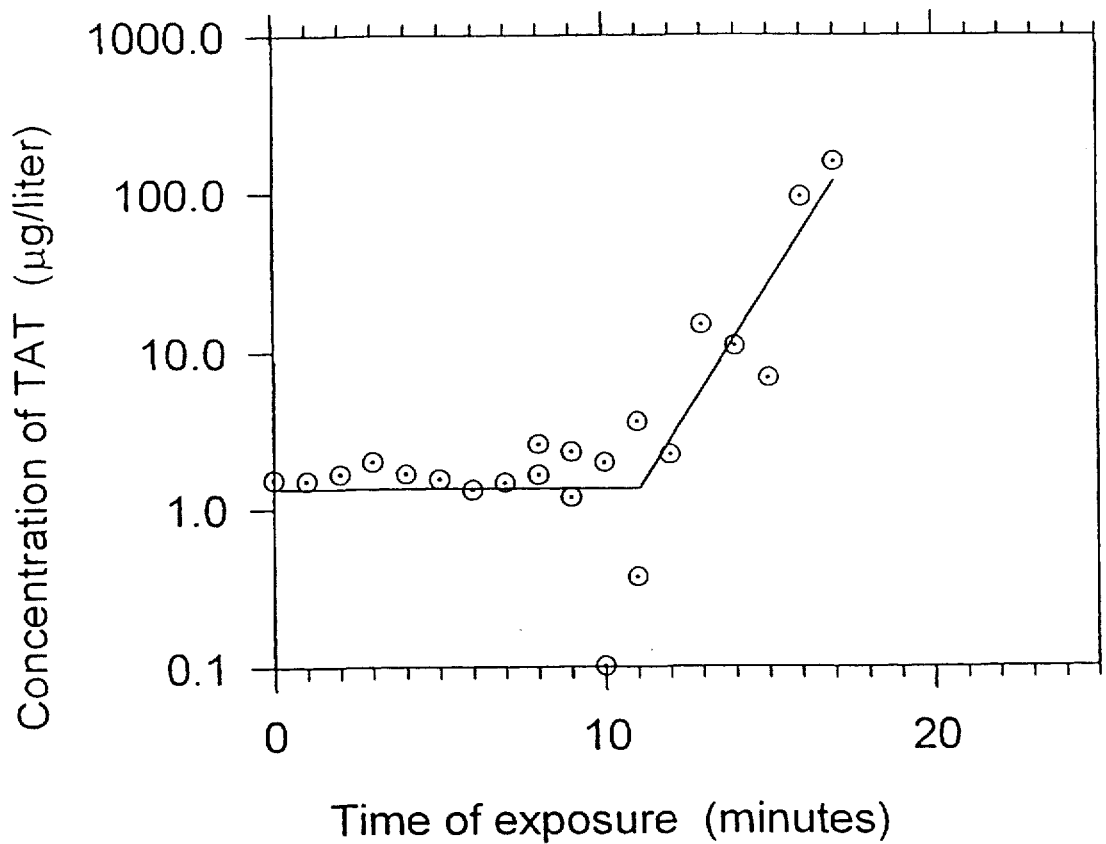
Figure 5D:
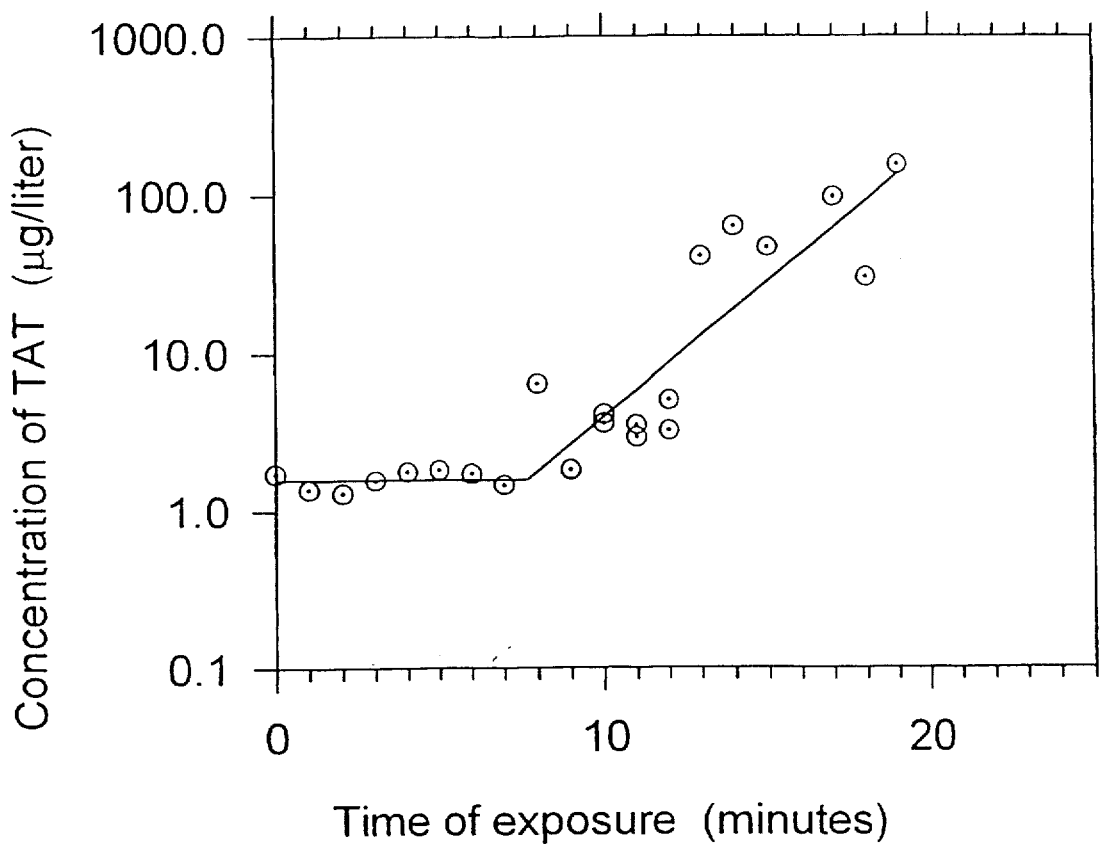
Figure 5E:
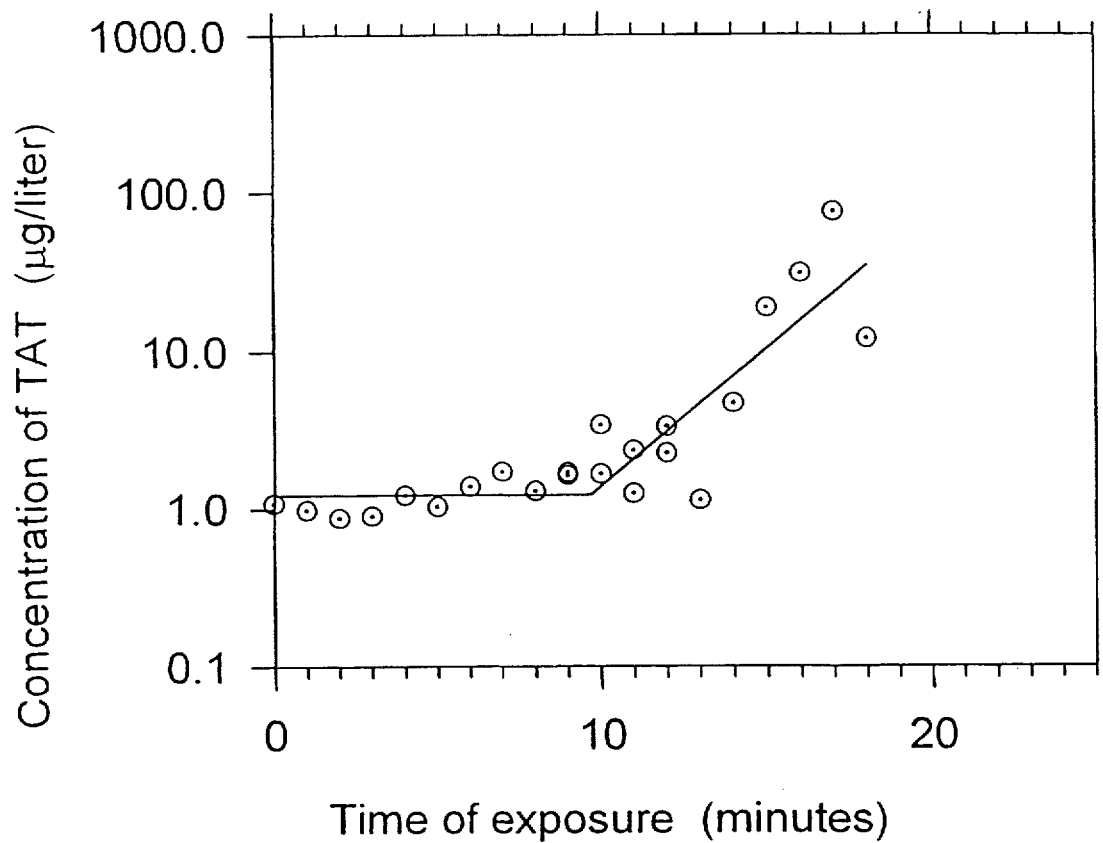
Figure 5F:
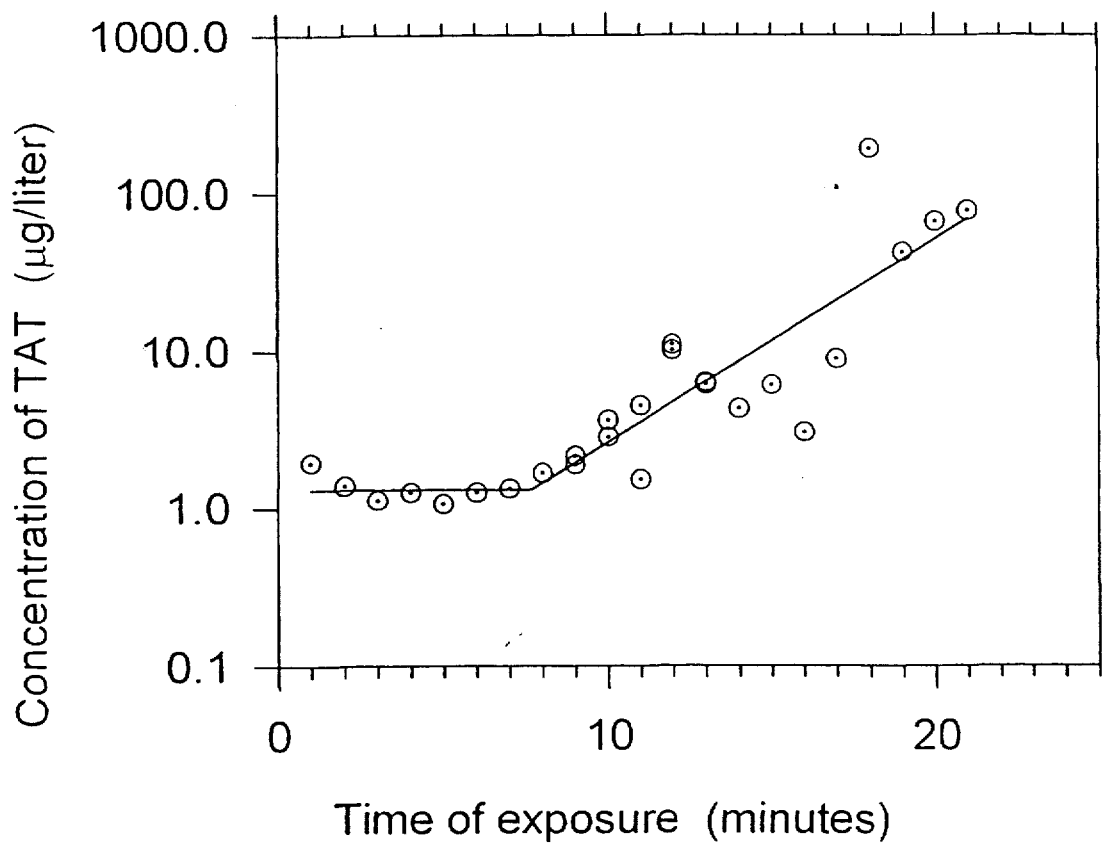
Figure 5G:
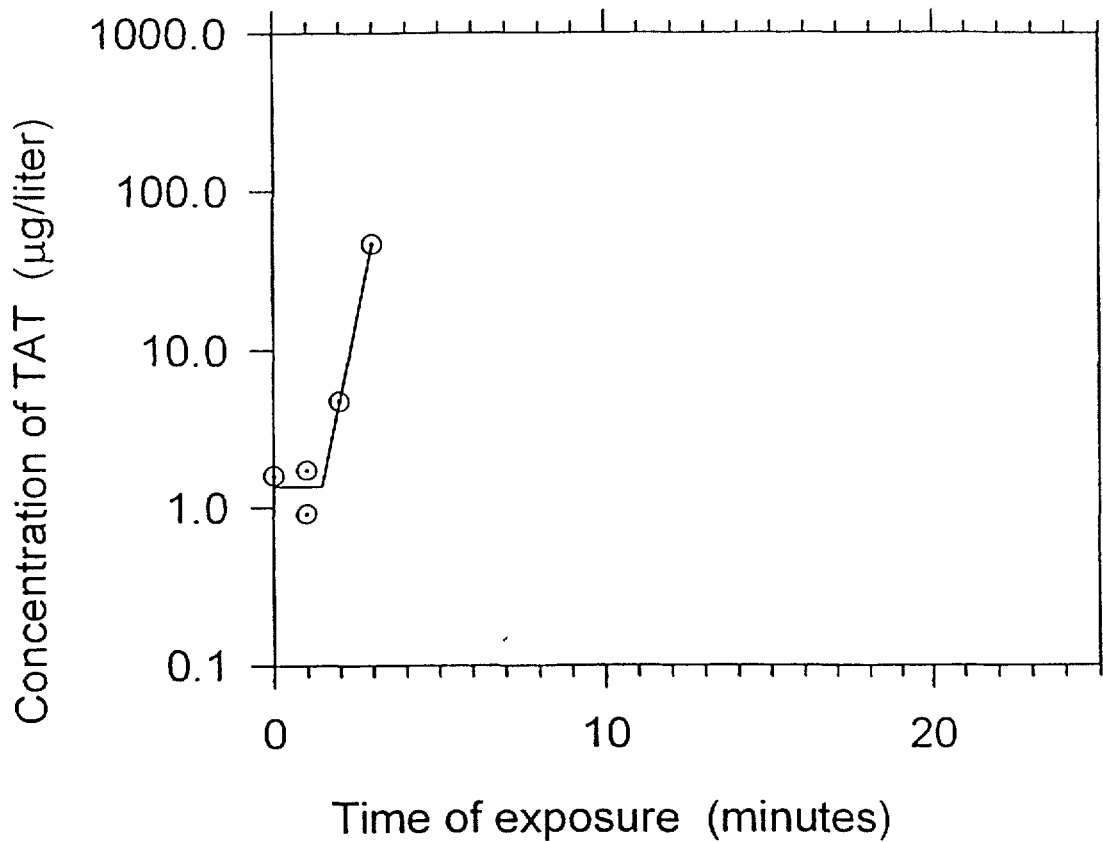
Figure 6:
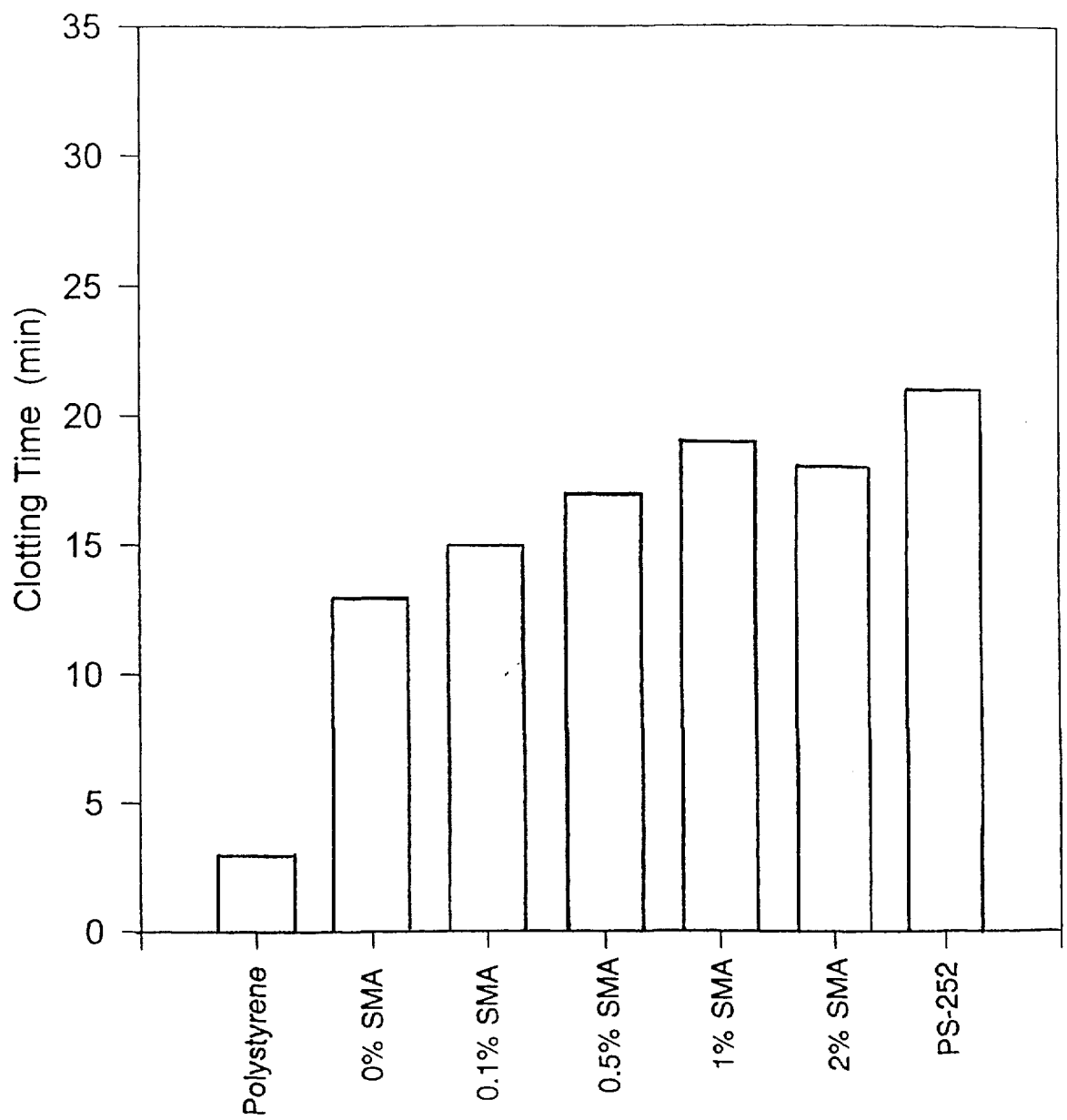
Figure 7:
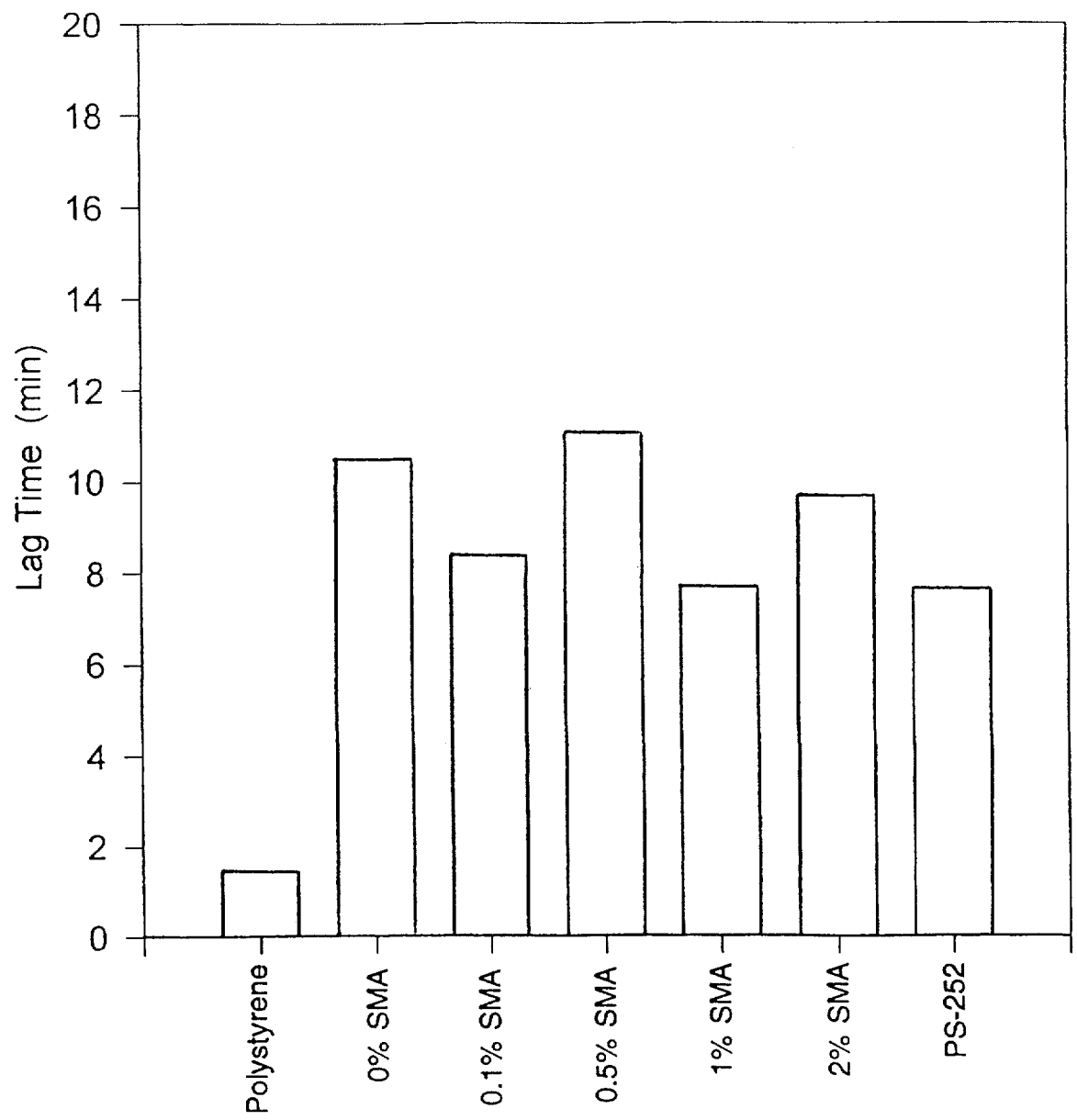
Figure 8:
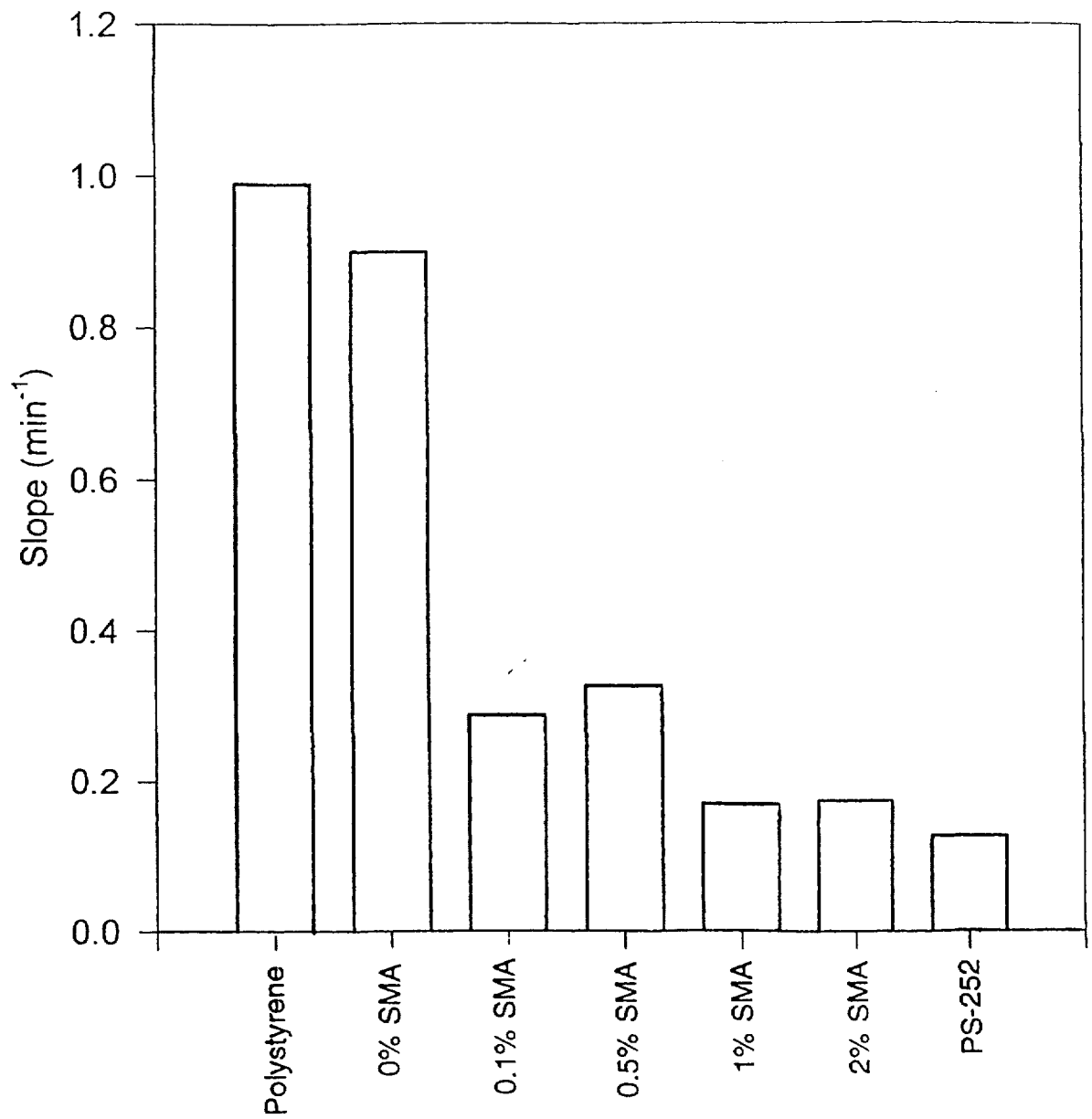

As shown in FIG. 6, the addition of SMA-423 coatings to the surface of 316L stainless steel produces a significant increase in the clotting time of recalcified human blood exposed to these surfaces. The clotting time increases with increasing concentration of SMA in the clotting solution. As shown in FIG. 7, the coated and uncoated stainless steel surfaces do not promote contact-phase activation of the intrinsic coagulation cascade, consistent with the results of the kallikrein-like activity assay (Example 4). By coating 316L stainless steel with SMA-423, the rate of the exponential increase of TAT in recalcified human blood is reduced in a dose dependent manner. SMA coatings improve the thromboresistance of the stainless steel surface in a dose dependent manner, with 1% and 2% SMA-423 coatings providing the highest thromboresistance.

EXAMPLE 6

Platelet and leukocyte compatibility studies. Whole blood (WB) of human volunteers was subjected to surface contact in tubing of various test materials as described in detail below. After one hour of contact, the blood was removed for analysis of platelet count as a measure of total platelet loss, and of microparticle release and percentages of platelets positive for P-selectin as measures of platelet activation. Analysis of platelet-leukocyte association, as an indicator of platelet activation induced by contact with test material, was carried out by measuring the platelet GPIIb antigen associated with leukocytes in a fluorescence-activated cell sorter. Leukocyte activation was assessed by measuring any loss of L-selectin and CD11b expression. The data are shown in Table 2. See Gemmell, C. H. et al. (1995) J. Lab. Clin. Med. 125(2):276–287, incorporated herein by reference.

Platelet Preparation:

Whole blood from normal volunteers (4 individuals) was drawn into syringes pre-loaded with anticoagulant after discarding the first mL. For most experiments the anticoagulant, PPACK, a selective thrombin inhibitor at a final concentration of 60 µM was used. The calcium chelator, 5 mM EGTA for the metal ion chelator, 5mM EDTA were also used as anticoagulants. All syringes were pre-warmed to 37° C. and the whole blood was immediately Blood Material Contact:

As shown in FIG. 9, fresh whole blood was added to tubes (25 cm L, 1.57 mm ID) whose ends were connected to two arms extending from the sides of a rocking platform (13 oscillations per minute). Ignoring the abrupt change in flow direction the maximum wall shear rate was less than 25 sec$^{-1}$. Both ends of the test segment terminated in Silastic segments (1.57 mm ID, 5 cm L) and at any given time 92% of the blood was within the test segment. For each experiment, a resting whole blood sample (0.5 ml) was set aside in a sealed microcentrifuge tube for one hour at 37° C. At the conclusion of the test, the 525 µl of whole blood within the tube was displaced, avoiding an air interface, with 150 µl of Hepes-Tyrodes buffer (HTB:137 mM NaCl, 2.7 mM KCl, 16 mM NaHCO$_3$, 5 mM MgCl$_2$, 3.5 mM Hepes, 1 g/L glucose, 2 g/L bovine albumin, pH 7.4). At this time EDTA (5 mM final concentration) was added to samples (including resting blood sample) for determination of platelet count as well as flow cytometric analysis of platelet activation and microparticle formation. For flow cytometric analysis of platelet association with leukocytes the blood samples were analyzed without EDTA added.

In certain cases, to identify the potential putative platelet receptors involved in material induced platelet activation, unlabelled antibody to GPIb (AP1, capable of blocking the vWF binding site) or antibody to GPIIb/IIIa (A2A9, capable of blocking fibrinogen binding) at up to 100 µg/ml were added to whole blood prior to material contact. The tetrapeptide, RGDS at 1 mg/ml was also sometimes added to inhibit ligand binding to GPIIb/IIIa. Three materials: polyvinyl alcohol hydrogel, polyethylene (Intramedic PE), Silastic™ (Dow Corning) were tested for times up to one hour at 37° C. and up to 9 tubes were tested simultaneously. Polyvinyl alcohol hydrogel coating onto oxidized PE was prepared as previously described by glutaraldehyde cross linking (Cholakis, C. H. et al. (1989) J. Biomed. Mater. Res. 23:417–441).

Flow Cytometry:

Samples were analyzed on a Becton Dickinson FACScan flow cytometer (Mountain View, Calif). For platelet analysis the light scatter and fluorescence channels were set at logarithmic gain. Two color analysis was used to determine the degree of α-granule release (P-selectin; KC4.1) and GPIIb/IIIa receptor activation (PAC-1, 9F9). Five μl samples of whole blood were diluted 10 fold with HTB and saturating concentrations of antibodies were added. After a 20 minute incubation samples were fixed with 1% paraformaldehyde. A minimum of 5,000 platelet events were acquired by gating on flow cytometric events within a single intact platelet window defined by light scatter characteristics and positive for FITC labelled platelet specific antibodies (GPIb or GPIIb/IIIa). The presence of the PE labelled activation specific antibody (KC4.1, PAC-1, 9F9) was used to determine the percentage of activated platelets. In addition, the arbitrary fluorescent intensity of the activated platelet population as well as the total fluorescent signal were recorded.

Platelet specific events, including microparticles, were identified by gating on GPIIb/IIIa (FITC-P2) or GPIb (FITC-AP1) positive events and microparticles were distinguished by forward scatter size analysis. The forward scatter cut off was set to the immediate left of the single intact platelet population of a resting whole blood sample, and very minor adjustments are required from day to day due to instrument variability. The concentration of microparticles was estimated by multiplying the single intact platelet count (determined in a WB sample containing EDTA so that all aggregates and platelet/leukocytes could be disrupted) by the percentage of platelet events (platelets and microparticles) falling into the microparticle window as assessed by flow cytometry. The Coulter counter's platelet gates are between 2 and 30 fl approximately, thus indicating that platelets counted are between 1.5 and 3.8 μm, if one assumes a spherical shape. It is possible that some large microparticles could be counted as single platelets using the Coulter counter. Using fluorescent beads (3, 2, 1, 0.46, 0.23 and 0.14 μm, Polysciences Inc.) we have shown that our microparticles are a heterogeneous population ranging in size from 0.1 to 0.8 μm. 5,000 positive platelet events were analyzed and microparticles reported as a percentage of total platelet events.

To determine the percentage of leukocytes with bound platelet(s) saturating concentrations of PE-anti-CD45 and FITC-P2 (anti-GPIIb/IIIa) were added to diluted (1:10) whole blood samples (5 μL) and incubated for 20 minutes. Samples were then diluted, fixed and analyzed. Acquisition was gated to include only those events positive for PE-anti-CD45 MoAb, the pan leukocyte marker. The second color (FITC) was used to determine the linearized fluorescent intensity of the platelet (anti-GPIIb/IIIa) signal associated with leukocytes. The background FITC fluorescence associated with leukocytes was determined from samples containing 10 mM EDTA, so that all platelets would be dissociated from leukocytes and from a FITC labelled irrelevant monoclonal antibody (HL1212), against a factor IX epitope.

Significant differences in response to the test materials were noted in the measurement of platelet loss (Table 2, column labeled "Platelet Count.") The presence of SMA either as coating or incorporated into the polymer dramatically reduced platelet loss after contact with polyvinylchloride (PVC) or polypropylene surfaces. The loss of platelets from PVC surfaces compounded with SMA was similar to that observed for Silastic (Trademark, Dow Chemical Co., Midland, Mich.), the negative control. Polypropylene surfaces caused a dramatic (69%) loss of platelets and the presence of SMA, either compounded or coated, substantially improved (decreased) platelet loss, to the extent that performance was better than untreated polyethylene.

For all surfaces, there was minimal evidence of bulk platelet release, as assessed by the low percentage of platelets 35 positive for P-selectin (α-granule release). The percentage of microparticles after surface contact was only marginally above background for PVC compounded with SMA and for Silastic™, suggesting a very low degree of platelet activation. PVC, polyethylene and polypropylene caused elevated microparticle formation, with polypropylene causing the greatest activation. The presence of SMA reduced the extent of microparticle formation.

Analysis of leukocyte activation revealed minimal upregulation of CD11b or L-selectin with any of the tested surfaces. The presence of SMA had no deleterious effect, however.

EXAMPLE 7

A polycarbonate disc was coated in a 1% solution of SMA-423 in Arcosolve PM. The disc was then irradiated in a Philips X-ray Fluorescence Spectrometer fitted with a chromium anode and operated at 60 KV and 50 MA. Part of the disc was masked by a copper ring so that it received no irradiation. The other part of the disc received a dose of 12 Mrads. The disc was then washed in ethanol at 45° C. which is known to be a good solvent for SMA-423. Retention of SMA-423 was measured by before and after comparison of XRF intensity ratios. The results are shown in the following table:

| Sample | % Retention of SMA-423 |
| --- | --- |
| Non Irradiated Coating | 0% |
| Irradiated Coating | 50% |

In a procedure identical to that just described, a stainless steel disc was coated with SMA-423. The results of washing in 45° C. ethanol are shown in the following table:

| Sample | % Retention of SMA-423 |
| --- | --- |
| Non Irradiated Coating | 0% |
| Irradiated Coating | 56% |

The teachings of the present invention provide for a new approach to fabricating biocompatible surfaces using coating materials. Besides the base polymers, metals and LSL coatings specifically exemplified, other base polymers, metals and LSL coatings are intended as within the scope of the invention, based on the teachings herein. Other coating procedures as known in the art can be employed. Other materials may be included in addition to the LSL copolymers, to incorporate other desired properties or to further enhance biocompatibility, all as understood in the art.

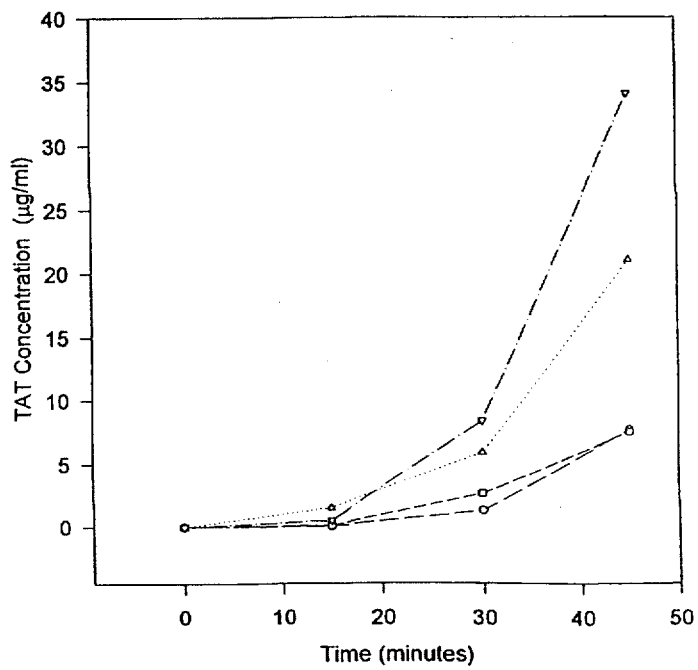

We claim:

1. A polymeric article having a base polymer and a biocompatible coating thereon comprising a polylactone-polysiloxane-polylactone triblock copolymer, said coating having a relative surface concentration sufficient to provide an X-ray fluorescence intensity ratio in the range 0.1 to 0.25.

2. A polymeric article according to claim 1 wherein the X-ray fluorescence intensity ratio is in the range 0.14 to 0.22.

3. A polymeric article according to claim 1 wherein said base polymer is a polypropylene membrane.

4. A polymeric article according to claim 1 wherein said base polymer is a polyethylene membrane.

5. A polymeric article according to claim 1 wherein the triblock copolymer is a polycaprolactone-polysiloxane-polycaprolactone copolymer.

6. A polymeric article according to claim 5 wherein the triblock copolymer comprises polycaprolactone blocks having each a nominal molecular weight in the range 1000 to 10,000 and a polysiloxane block having a nominal molecular weight in the range 1000 to 5000.

7. A polymeric article according to claim 6 wherein the triblock copolymer comprises polycaprolactone blocks having a nominal molecular weight of 2000 and a polysiloxane block having a nominal molecular weight in the range 2000–3000.

8. A polymeric article having a base polymer and a biocompatible coating thereon comprising a polylactone-polysiloxane-polylactone triblock copolymer, said coating having a relative surface concentration sufficient to provide an X-ray fluorescence intensity ratio in the range 0.02 to 0.35.

9. A polymeric article according to claim 8 wherein the X-ray fluorescence intensity ratio is in the range 0.05 to 0.25.

10. A polymeric article according to claim 8 wherein the X-ray fluorescence intensity ratio is in the range 0.16 to 0.20.

11. A polymeric article according to claim 8 wherein said base polymer is a polypropylene membrane.

12. A polymeric article according to claim 8 wherein said base polymer is a polyethylene membrane.

* * * * *

UNITED STATES PATENT AND TRADEMARK OFFICE
CERTIFICATE OF CORRECTION

PATENT : 5,643,681

DATED : July 1, 1997

INVENTOR(S) : Marc Voorhees et al

It is certified that error appears in the above-identified patent and that said Letters Patent is hereby corrected as shown below:

In the Drawings, Figs. 2, 5E, 5F, 5G, 6 and 7, should be deleted and substitute therefore the corrected Figs. 2, 5E, 5F, 5G, 6 and 7, as shown on the attached pages.

Column 1, line 5, after "1994" please add --, now abandoned--.

Column 9, line 20, please delete "15-14 30" and replace with --15-30--.

Column 10, line 46, please delete "25:29-298" and replace with --25:293-298--.

Column 10, line 57, please delete "6:851-859" and replace with --26:851-859--.

Column 11, line 50, please delete "8:475-496" and replace with --18:475-496--.

Column 16, line 1, please delete "35".

Signed and Sealed this

Eighth Day of September, 1998

BRUCE LEHMAN

*Attest:*

*Attesting Officer*   *Commissioner of Patents and Trademarks*

UNITED STATES PATENT AND TRADEMARK OFFICE
CERTIFICATE OF CORRECTION

PATENT NO. : 5,643,681
DATED : Jul. 1, 1997
INVENTOR(S) : Marc Voorhees, et al.

It is certified that error appears in the above-identified patent and that said Letters Patent is hereby corrected as shown below:

The title page should be deleted to appear as per attached title page.

Please delete drawing sheets 1-14 and substitute drawing sheets 1-14 as per attached.

Signed and Sealed this

Third Day of November, 1998

Attest:

BRUCE LEHMAN

Attesting Officer

Commissioner of Patents and Trademarks

United States Patent [19]
Voorhees et al.

[11] Patent Number: 5,643,681
[45] Date of Patent: Jul. 1, 1997

[54] BIOCOMPATIBLE COATED ARTICLE

[75] Inventors: Marc Voorhees, Arvada; Lloyd Forrestal, Boulder, both of Colo.; Harold Fisher, Charlotte, N.C.

[73] Assignee: Cobe Laboratories, Inc., Lakewood, Colo.

[21] Appl. No.: 473,723

[22] Filed: Jun. 7, 1995

Related U.S. Application Data

[63] Continuation of Ser. No. 227,955, Apr. 15, 1994, abandoned.

[51] Int. Cl.$^6$ ................ B32B 27/32; B32B 27/36
[52] U.S. Cl. ................ 428/483; 428/315.5; 428/315.9; 428/319.7; 428/447; 428/451; 428/480
[58] Field of Search .................. 428/308.4, 315.5, 428/315.9, 319.3, 319.7, 423.7, 425.5, 447, 451, 480, 483

[56] References Cited

U.S. PATENT DOCUMENTS

| | | | |
|---|---|---|---|
| 3,651,616 | 3/1972 | Blanchard et al. | 55/16 |
| 4,636,552 | 1/1987 | Gay et al. | 525/63 |
| 4,663,413 | 5/1987 | Ward et al. | 528/26 |
| 4,675,361 | 6/1987 | Ward, Jr. et al. | 525/92 |
| 4,872,867 | 10/1989 | Joh | 604/269 |
| 4,929,510 | 5/1990 | Ruckenstein et al. | 428/520 |
| 4,970,765 | 11/1990 | Canivenc et al. | 528/15 |
| 5,179,142 | 1/1993 | Ono et al. | 524/35 |

FOREIGN PATENT DOCUMENTS

| | | |
|---|---|---|
| 19 44 969 | 3/1970 | Germany. |
| 42 17 165 | 8/1993 | Germany. |

OTHER PUBLICATIONS

Zisman, W.A. (1964) *Adv. Chem. Ser.* 43.
Lovinger et al. (1993) "Morphology and Properties of Poly-caprolactone–Poly(dimethyl siloxane)–Polycaprolactone Triblock Copolymers," *J. Polymer Sci. Part B (Polymer Physics)* 31:115–123.
Gemmell et al. (1995) *J. lab. Clin. Med.* 125:276–287.
Clarson and Semlyn (eds.) (1993) *Siloxane Polymers*, "Radiation Cross-Linking of Siloxanes," pp. 606–609.

*Primary Examiner*—D. S. Nakarani
*Attorney, Agent, or Firm*—Greenlee, Winner and Sullivan, P.C.

[57] ABSTRACT

The biocompatibility of polymeric and metallic articles used in contact with blood can be substantially improved by coating the articles as described. The coating materials are triblock copolymers of the polylactone-polysiloxane-polylactone type. Optimum biocompatibility is provided by a coating of optimum surface concentration. Porous membranes can be coated as described, providing improved biocompatibility of blood oxygenators, hemodialyzers and the like.

12 Claims, 14 Drawing Sheets